United States Patent
Worrell et al.

(10) Patent No.: US 10,226,274 B2
(45) Date of Patent: Mar. 12, 2019

(54) ULTRASONIC SURGICAL INSTRUMENT WITH ARTICULATION JOINT HAVING PLURALITY OF LOCKING POSITIONS

(71) Applicant: Ethicon Endo-Surgery, LLC, Guaynabo, PR (US)

(72) Inventors: Barry C. Worrell, Centerville, OH (US); Disha V. Labhasetwar, Cincinnati, OH (US); Benjamin D. Dickerson, Cincinnati, OH (US); Michael R. Lamping, Cincinnati, OH (US); Daniel J. Mumaw, Liberty Township, OH (US); David T. Martin, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 461 days.

(21) Appl. No.: 14/688,234

(22) Filed: Apr. 16, 2015

(65) Prior Publication Data

US 2016/0302817 A1 Oct. 20, 2016

(51) Int. Cl.
*A61B 17/32* (2006.01)
*A61N 7/00* (2006.01)
(Continued)

(52) U.S. Cl.
CPC ........ *A61B 17/320092* (2013.01); *A61N 7/00* (2013.01); *A61B 2017/00327* (2013.01);
(Continued)

(58) Field of Classification Search
CPC .. A61B 17/320068; A61B 2017/00323; A61B 2017/00327; A61B 2017/00314; A61B 2017/2946
See application file for complete search history.

(56) References Cited

U.S. PATENT DOCUMENTS 5,297,443 A * 3/1994 Wentz .................. B05B 15/066
446/27
5,322,055 A 6/1994 Davison et al.
(Continued)

FOREIGN PATENT DOCUMENTS

EP 2 901 948 A1 8/2015
WO WO 2014/050783 A1 4/2014

OTHER PUBLICATIONS

U.S. Appl. No. 14/258,179, filed Apr. 22, 2014.
(Continued)

*Primary Examiner* — Alexander Orkin
(74) *Attorney, Agent, or Firm* — Frost Brown Todd LLC

(57) ABSTRACT

An apparatus comprises a body assembly, a shaft, an acoustic waveguide, an articulation section, an end effector, an articulation drive assembly, and a locking feature. The shaft extends distally from the body assembly. The waveguide comprises a flexible portion. The articulation drive assembly is operable to drive articulation of the articulation section to thereby deflect the end effector from the longitudinal axis of the shaft. The articulation drive assembly comprises an actuator. The actuator is movable relative to the body assembly to drive articulation of the articulation section. The locking feature is in communication with the actuator. The locking feature is movable between an unlocked state and a locked state. The locking feature is configured to permit movement of the actuator relative to the body assembly in the unlocked state. The locking feature is configured to prevent movement of the actuator relative to the body assembly in the locked state.

5 Claims, 41 Drawing Sheets

(51) Int. Cl.
*A61B 17/00* (2006.01)
*A61B 17/29* (2006.01)
*A61B 18/00* (2006.01)

(52) U.S. Cl.
CPC .......... *A61B 2017/2925* (2013.01); *A61B 2017/2927* (2013.01); *A61B 2017/2946* (2013.01); *A61B 2018/00607* (2013.01)

(56) References Cited

U.S. PATENT DOCUMENTS

| | | | |
|---|---|---|---|
| 5,348,259 A * | 9/1994 | Blanco | A61B 17/115 227/19 |
| 5,413,107 A * | 5/1995 | Oakley | A61B 8/12 600/463 |
| 5,549,637 A * | 8/1996 | Crainich | A61B 17/29 606/170 |
| 5,649,955 A * | 7/1997 | Hashimoto | A61B 17/29 600/562 |
| 5,704,534 A | 1/1998 | Huitema et al. | |
| 5,762,067 A * | 6/1998 | Dunham | A61B 1/0052 600/148 |
| 5,766,196 A * | 6/1998 | Griffiths | A61B 17/29 600/564 |
| 5,836,960 A | 11/1998 | Kolesa et al. | |
| 5,873,873 A | 2/1999 | Smith et al. | |
| 5,897,523 A | 4/1999 | Wright et al. | |
| 5,938,616 A * | 8/1999 | Eaton | A61B 1/0052 600/446 |
| 5,980,510 A | 11/1999 | Tsonton et al. | |
| 5,989,264 A | 11/1999 | Wright | |
| 6,063,098 A | 5/2000 | Houser et al. | |
| 6,090,120 A | 7/2000 | Wright et al. | |
| 6,325,811 B1 | 12/2001 | Messerly | |
| 6,454,782 B1 | 9/2002 | Schwemberger | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 6,942,613 B2 * | 9/2005 | Ewers | A61B 1/0008 600/114 |
| 7,135,030 B2 | 11/2006 | Schwemberger et al. | |
| 7,621,930 B2 | 11/2009 | Houser | |
| 8,461,744 B2 | 6/2013 | Wiener et al. | |
| 8,591,536 B2 | 11/2013 | Robertson | |
| 8,623,027 B2 | 1/2014 | Price et al. | |
| 8,968,357 B2 | 3/2015 | Mueller | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 2003/0191516 A1 * | 10/2003 | Weldon | A61F 2/95 623/1.12 |
| 2003/0236493 A1 * | 12/2003 | Mauch | A61M 25/0136 604/95.04 |
| 2006/0058825 A1 * | 3/2006 | Ogura | A61B 17/32 606/169 |
| 2006/0079874 A1 | 4/2006 | Faller et al. | |
| 2006/0264787 A1 * | 11/2006 | Yamada | A61B 17/32006 601/2 |
| 2007/0191713 A1 | 8/2007 | Eichmann et al. | |
| 2007/0225641 A1 * | 9/2007 | Schneider | A61M 25/0136 604/93.01 |
| 2007/0282333 A1 | 12/2007 | Fortson et al. | |
| 2007/0282371 A1 * | 12/2007 | Lee | A61B 17/062 606/205 |
| 2008/0200940 A1 | 8/2008 | Eichmann et al. | |
| 2008/0308607 A1 * | 12/2008 | Timm | A61B 17/07207 227/176.1 |
| 2010/0174290 A1 * | 7/2010 | Wuebbeling | A61F 2/95 606/108 |
| 2010/0193566 A1 | 8/2010 | Scheib et al. | |
| 2012/0078247 A1 | 3/2012 | Worrell et al. | |
| 2012/0112687 A1 | 5/2012 | Houser et al. | |
| 2012/0116265 A1 | 5/2012 | Houser et al. | |
| 2013/0023868 A1 | 1/2013 | Worrell et al. | |
| 2013/0289592 A1 | 10/2013 | Stulen et al. | |
| 2014/0005701 A1 | 1/2014 | Olson et al. | |
| 2014/0005703 A1 | 1/2014 | Stulen et al. | |
| 2015/0080924 A1 | 3/2015 | Stulen et al. | |

OTHER PUBLICATIONS

U.S. Appl. No. 61/410,603, filed Nov. 5, 2010.
International Search Report and Written Opinion dated Jul. 28, 2016 for Application No. PCT/US2016/027661, 12 pgs.

* cited by examiner

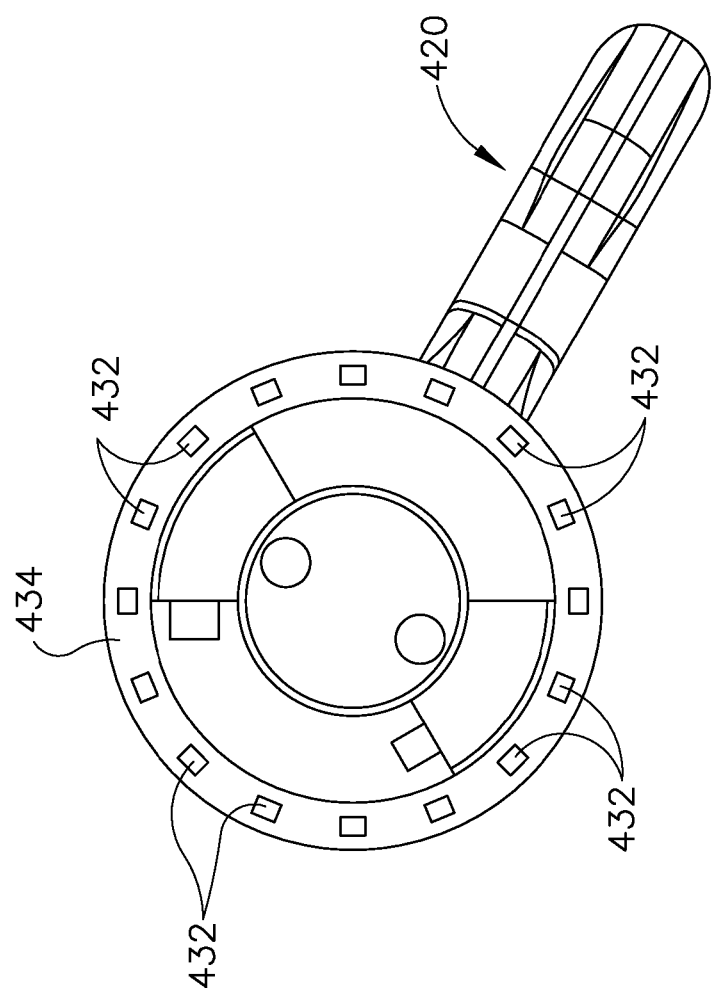

ULTRASONIC SURGICAL INSTRUMENT WITH ARTICULATION JOINT HAVING PLURALITY OF LOCKING POSITIONS

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, entitled "Surgical Instruments with Articulating Shafts," now U.S. Pat. No. 9,393,037, issued Jul. 19, 2016, the disclosure of which is incorporated by reference herein; U.S. Pub. No. 2014/0005703, entitled "Surgical Instruments with Articulating Shafts," published Jan. 2, 2014, now U.S. Pat. No. 9,408,622, issued Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, now U.S. Pat. No. 9,095,367, issued Aug. 4, 2015, the disclosure of which is incorporated by reference herein; U.S. Pub. No. 2015/0080924, entitled "Articulation Features for Ultrasonic Surgical Instrument," published Mar. 19, 2015, now U.S. Pat. No. 10,172,636, issued on Jan. 8, 2019, the disclosure of which is incorporated by reference herein; and U.S. patent application Ser. No. 14/258,179, entitled "Ultrasonic Surgical Device with Articulating End Effector," filed Apr. 22, 2014, was reverted to U.S. Provisional 62/176,880, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 16 a bottom plan view of a knob of the articulation control assembly of FIG. 15A;

Figure 1:
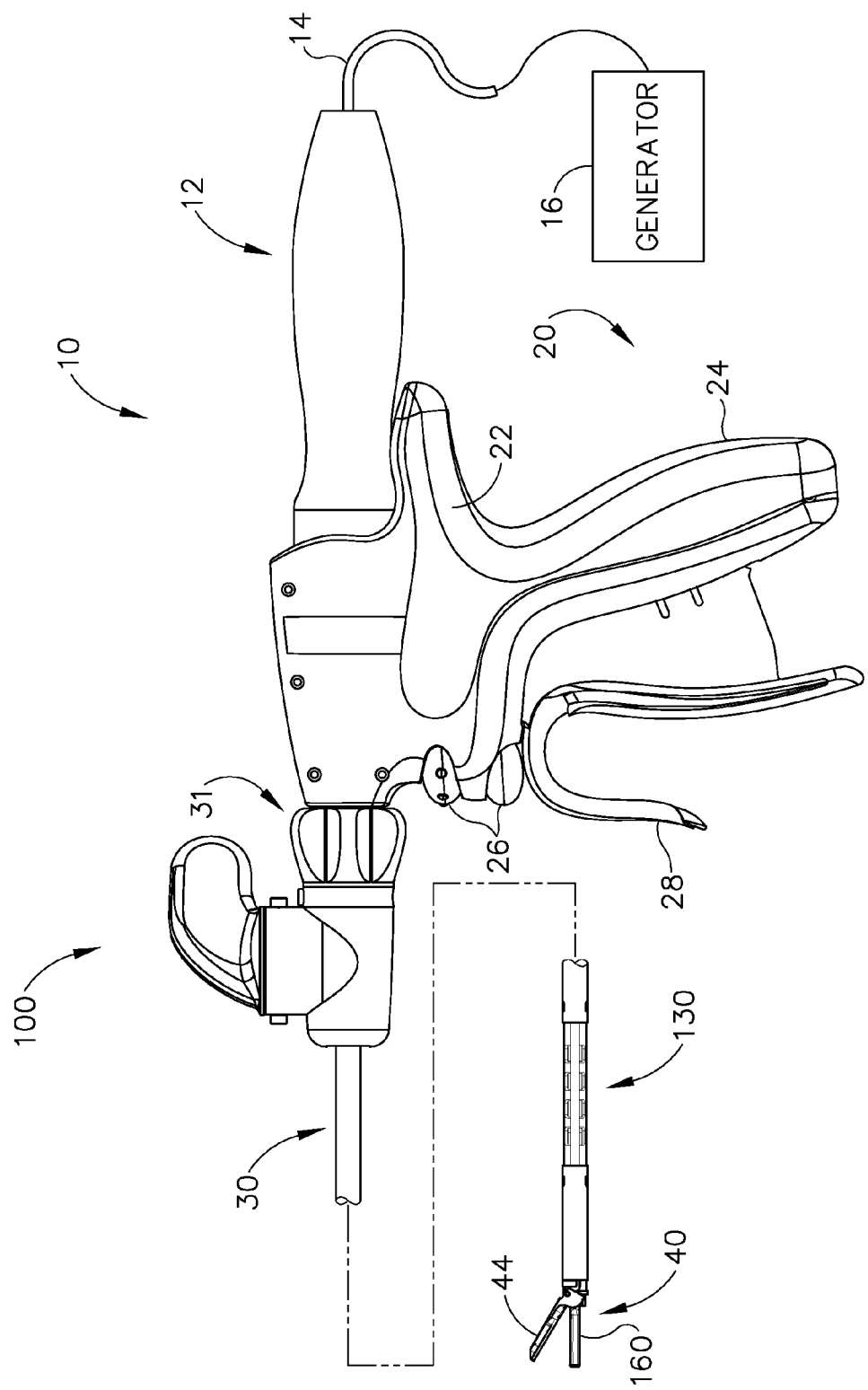
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No.

2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
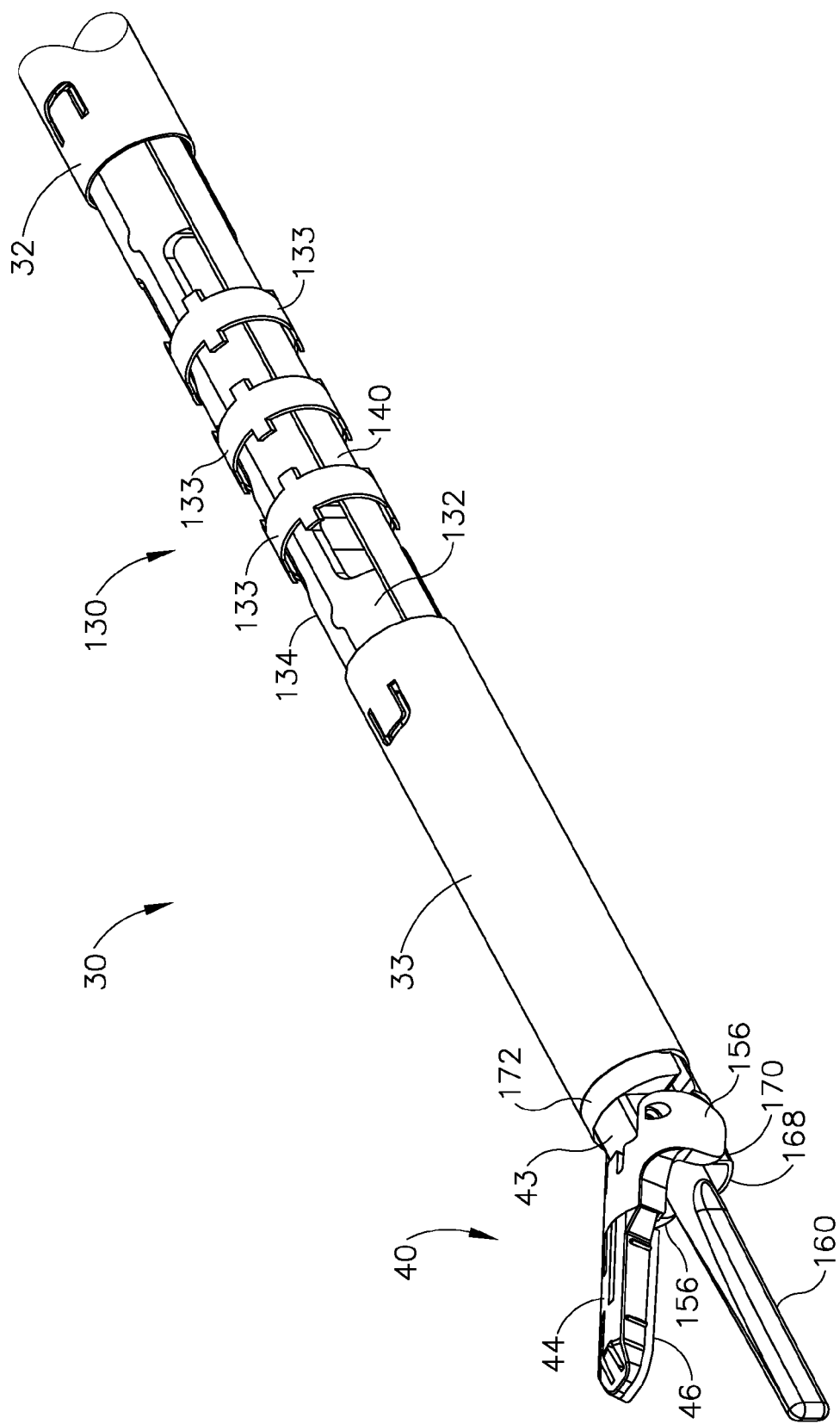
FIG. 2 depicts a perspective view of an articulation section of a shaft assembly and an end effector of the surgical instrument of FIG. 1.
Figure 3:
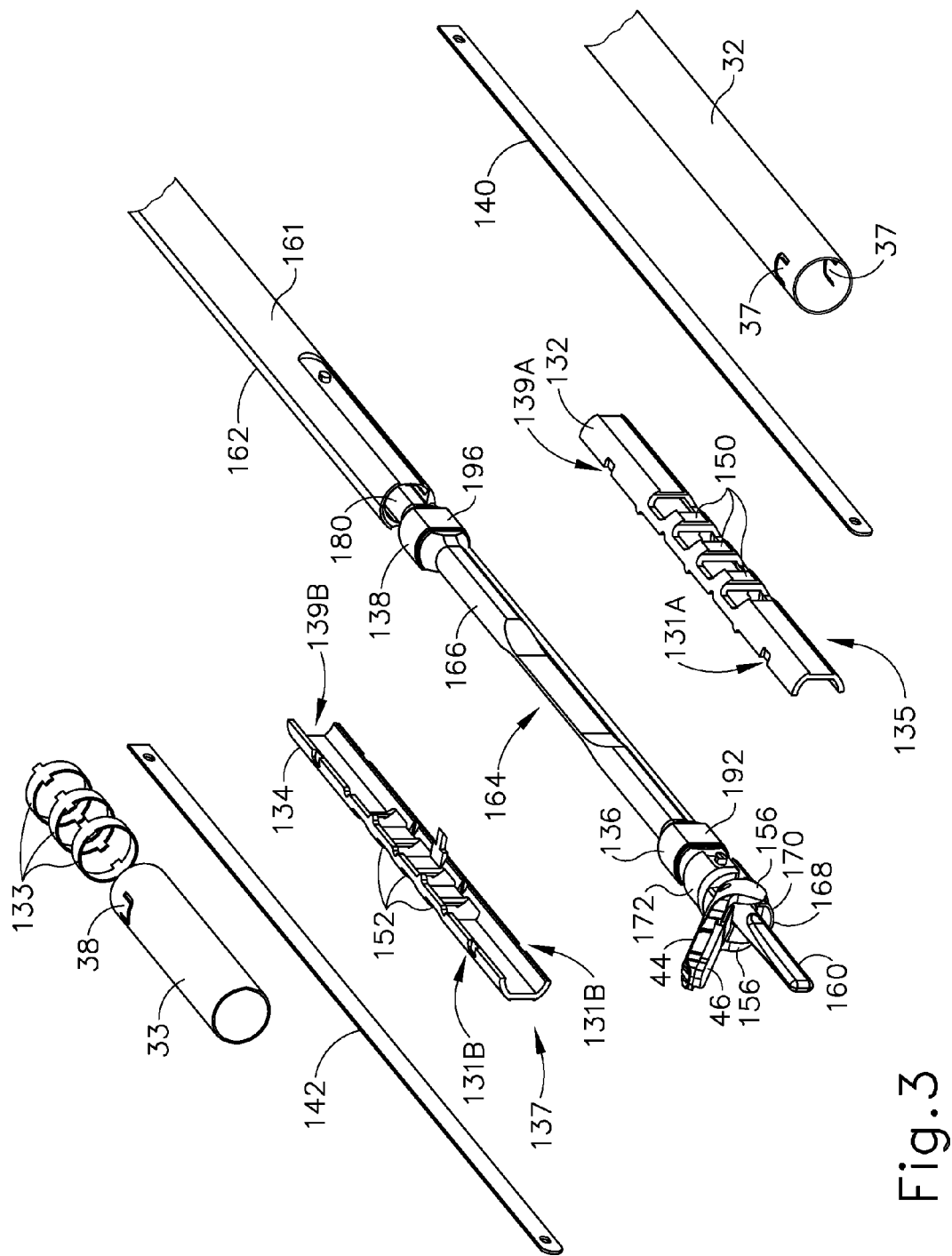
FIG. 3 depicts an exploded perspective view of an articulation section of the shaft assembly of FIG. 2.
Figure 4:
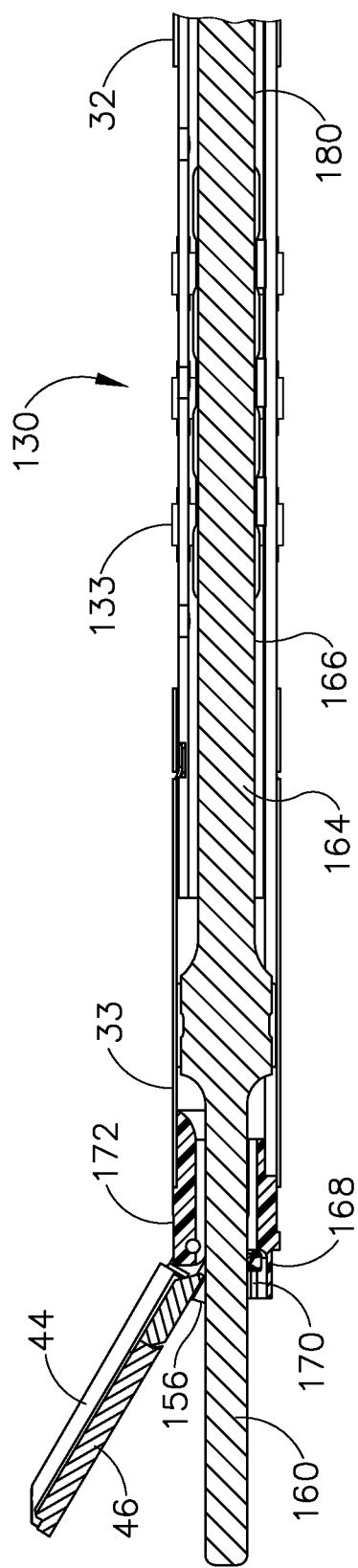
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

Figure 7:
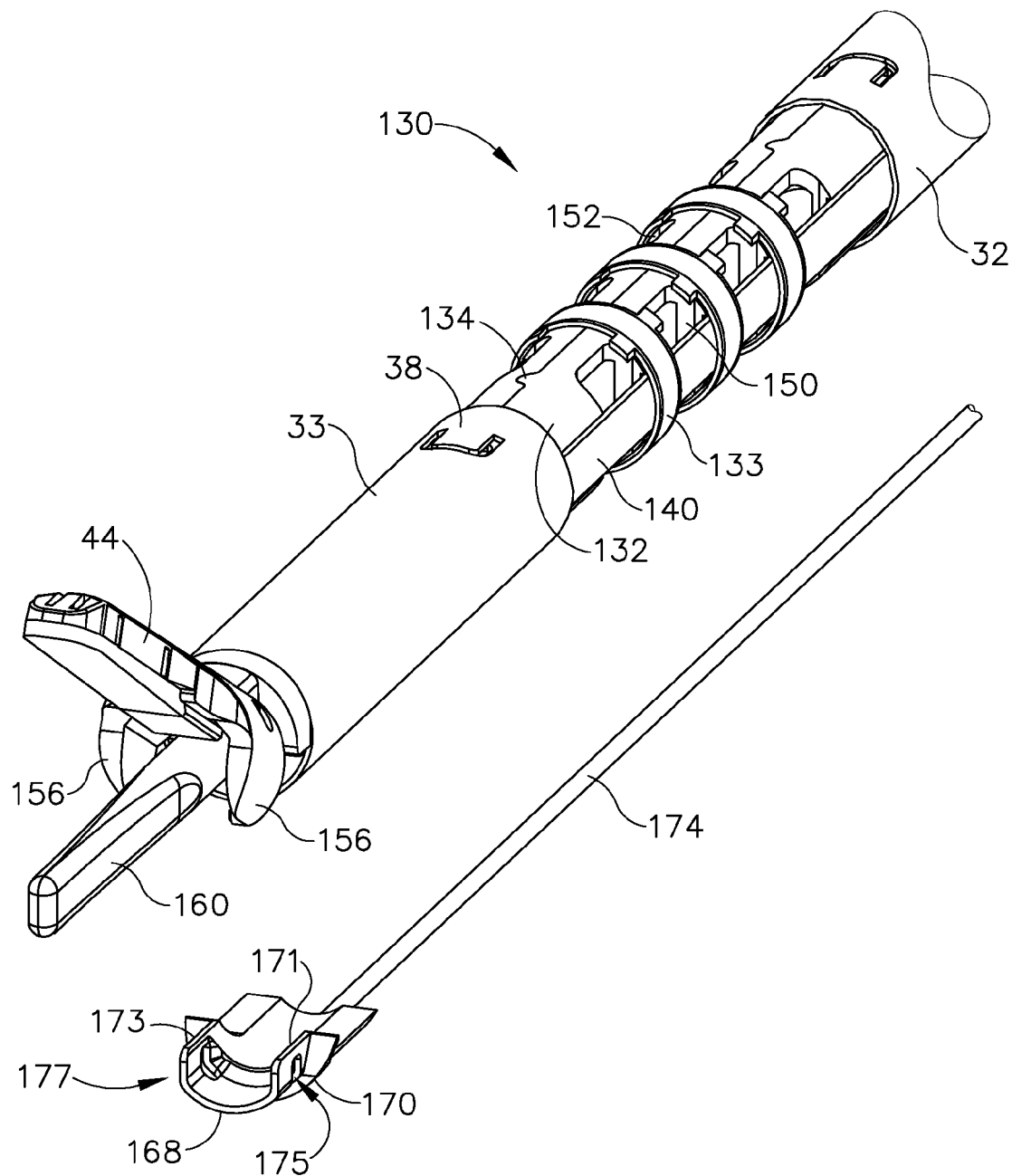
FIG. 7 depicts a partially exploded perspective view of the shaft assembly and end effector of FIG. 2.
Figure 8:
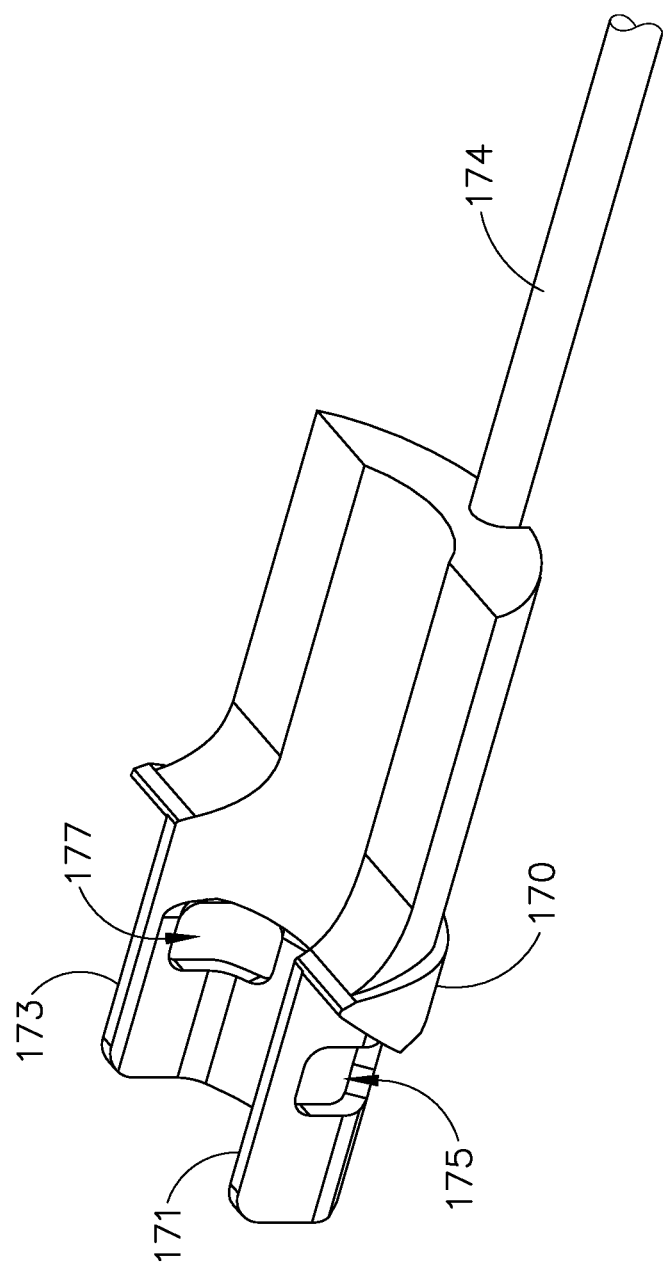
FIG. 8 depicts a perspective view of a distal collar and a drive cable of the shaft assembly of FIG. 2.

As best seen in FIGS. 7-8, a cable (174) is secured to lower distal shaft element (170). Cable (174) is operable to translate longitudinally relative to an articulation section (130) of shaft assembly (30) to selectively pivot clamp arm (44) toward and away from blade (160). In particular, cable (174) is coupled with trigger (28) such that cable (174) translates proximally in response to pivoting of trigger (28) toward pistol grip (24), and such that clamp arm (44) thereby pivots toward blade (160) in response to pivoting of trigger (28) toward pistol grip (24). In addition, cable (174) translates distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Figure 10A:
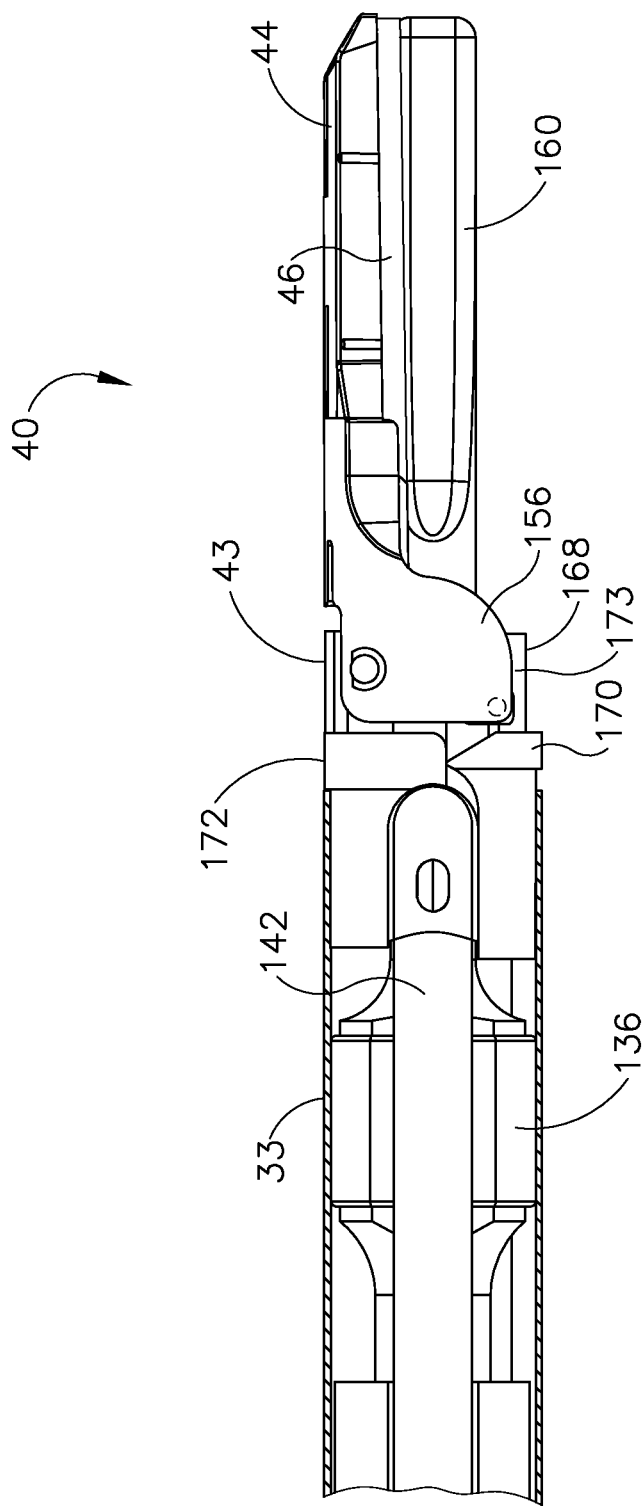
FIG. 10A depicts a side elevational view of the end effector and the distal portion of the shaft assembly of FIG. 2, with a clamp arm of the end effector in a closed position, and with an outer sheath shown in cross section to reveal components within the outer sheath.
Figure 10B:
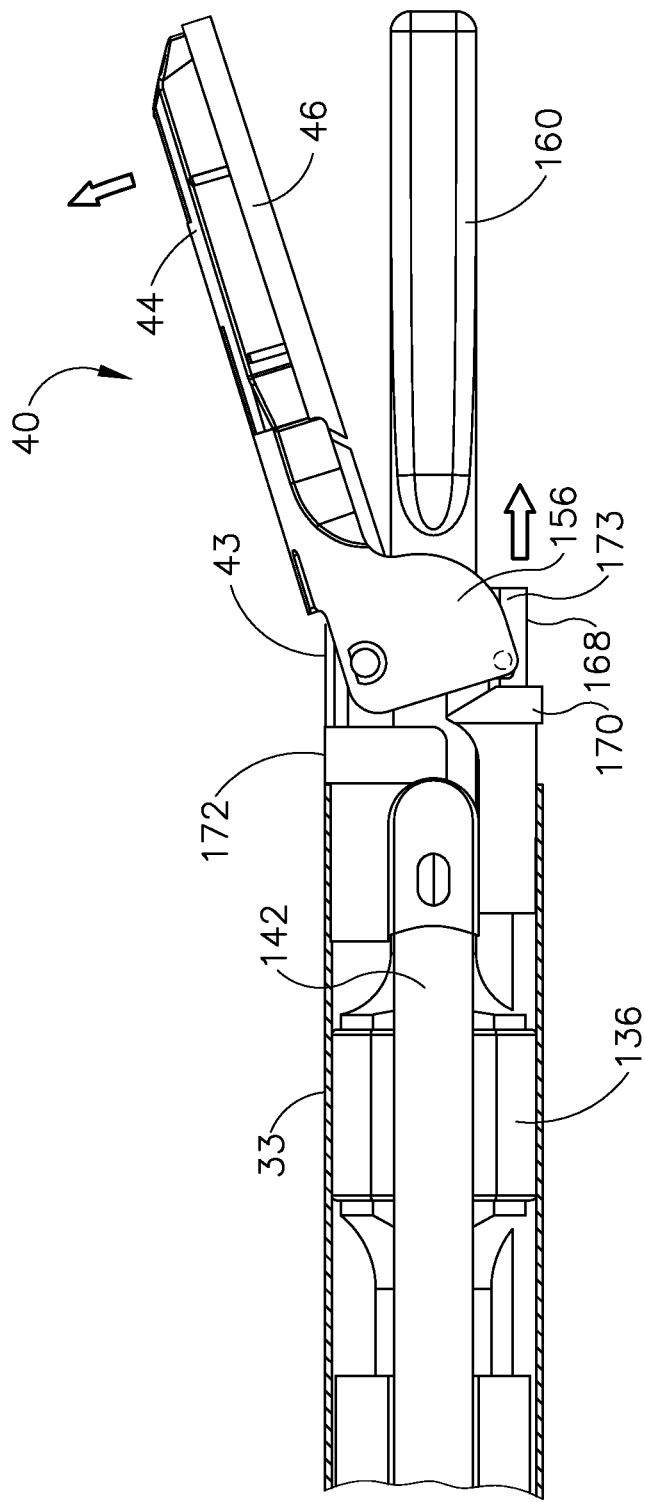
FIG. 10B depicts a side elevational view of the shaft assembly and end effector of FIG. 10A, with the clamp arm moved to a partially open position.
Figure 10C:
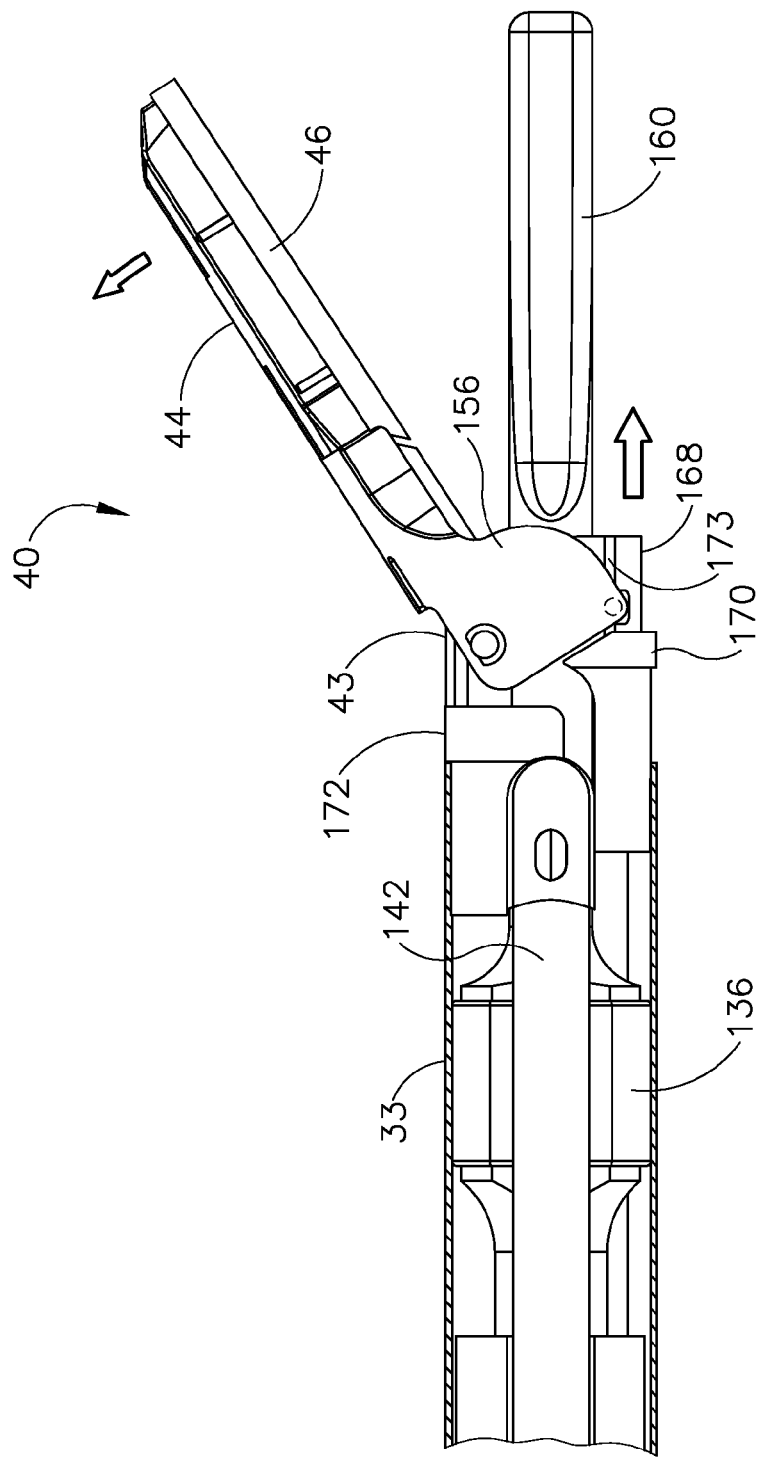
FIG. 10C depicts a side elevational view of the shaft assembly and end effector of FIG. 10A, with the clamp arm moved to a fully open position.

As shown in FIGS. 7-8, cable (174) is secured to a proximal end of lower distal shaft element (170). Lower distal shaft element (170) comprises a pair of distal flanges (171, 173) extending from a semi-circular base (168). Flanges (171, 173) each comprise a respective opening (175, 177). Clamp arm (44) is rotatably coupled to lower distal shaft element (170) via a pair of inwardly extending integral pins (41, 45). Pins (41, 45) extend inwardly from arms (156) of clamp arm (44) and are rotatably disposed within respective openings (175, 177) of lower distal shaft element (170). As shown in FIGS. 10A-10C, longitudinal translation of cable (174) causes longitudinal translation of lower distal shaft element (170) between a proximal position (FIG. 10A) and a distal position (FIG. 10C). Longitudinal translation of lower distal shaft element (170) causes rotation of clamp arm (44) between a closed position (FIG. 10A) and an open position (FIG. 10C).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). Transducer assembly (12) includes a set of piezoelectric discs (not shown) located proximal to a horn (not shown) of waveguide (180). The piezoelectric discs are operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, now U.S. Pat. No. 9,393,037, issued July, 19, 2016, and/or U.S. Pub. No. 2014/0114334, now U.S. Pat. No. 9,095,367, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

In the present example, the distal end of blade (160) is located at a position corresponding to an anti-node associated with resonant ultrasonic vibrations communicated through flexible portion (166) of waveguide (180), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-7, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, now U.S. Pat. No. 9,402,682, issued Aug. 2, 2016, the disclosure of which is incorporated by reference herein. As another merely illustrative example, articulation section (130) may be configured in accordance with one or more teachings of U.S. Pub. No. 2014/0005701, now U.S. Pat. No. 9,393,037, issued Jul. 19, 2016, and/or U.S. Pub. No. 2014/0114334, now U.S. Pat. No. 9,095,367, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
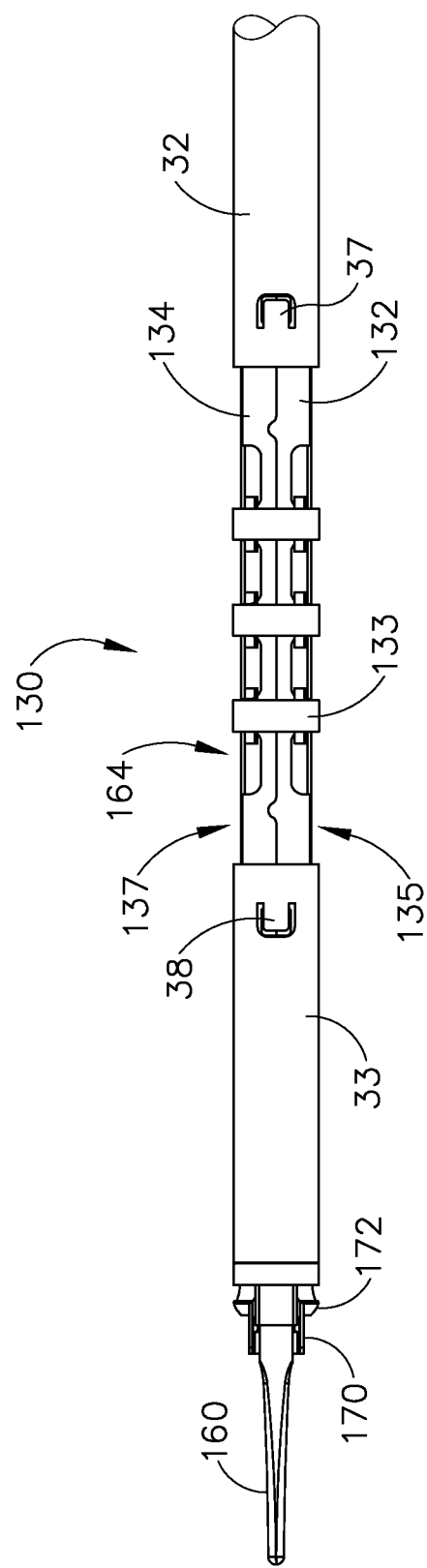
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
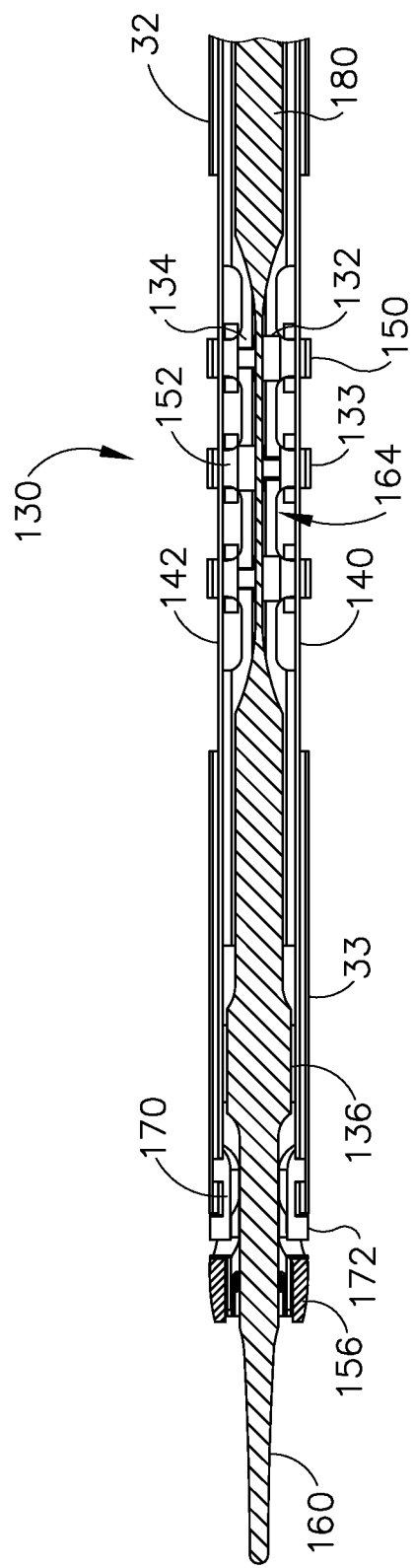
FIG. 6A depicts a cross-sectional top view of the shaft assembly and end effector of FIG. 2 in a straight configuration.
Figure 6B:
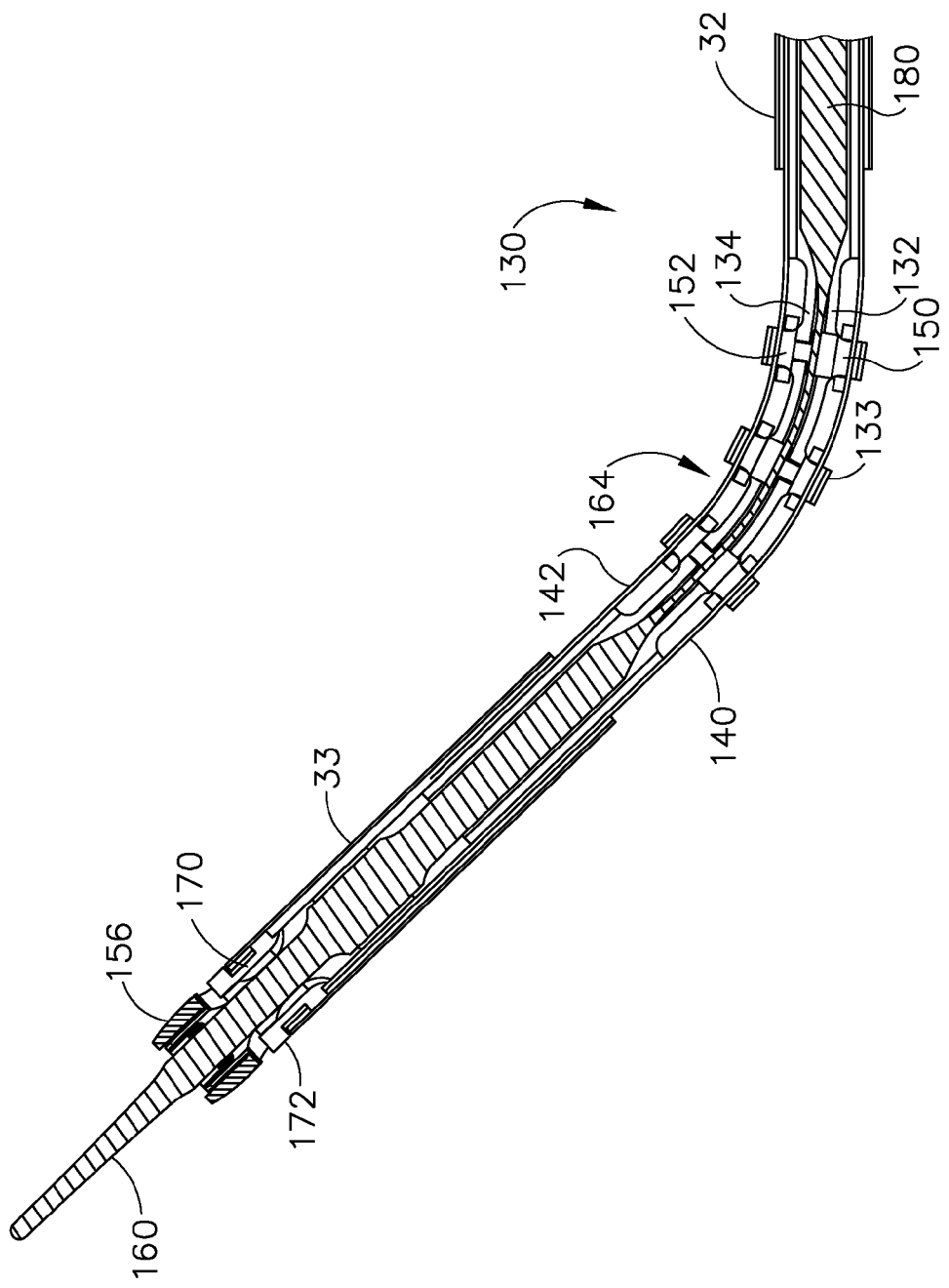
FIG. 6B depicts a cross-sectional top view of the shaft assembly and end effector of FIG. 2 in an articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32); while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," filed Apr. 23, 2013 published Oct. 31, 2013, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

Figure 9:
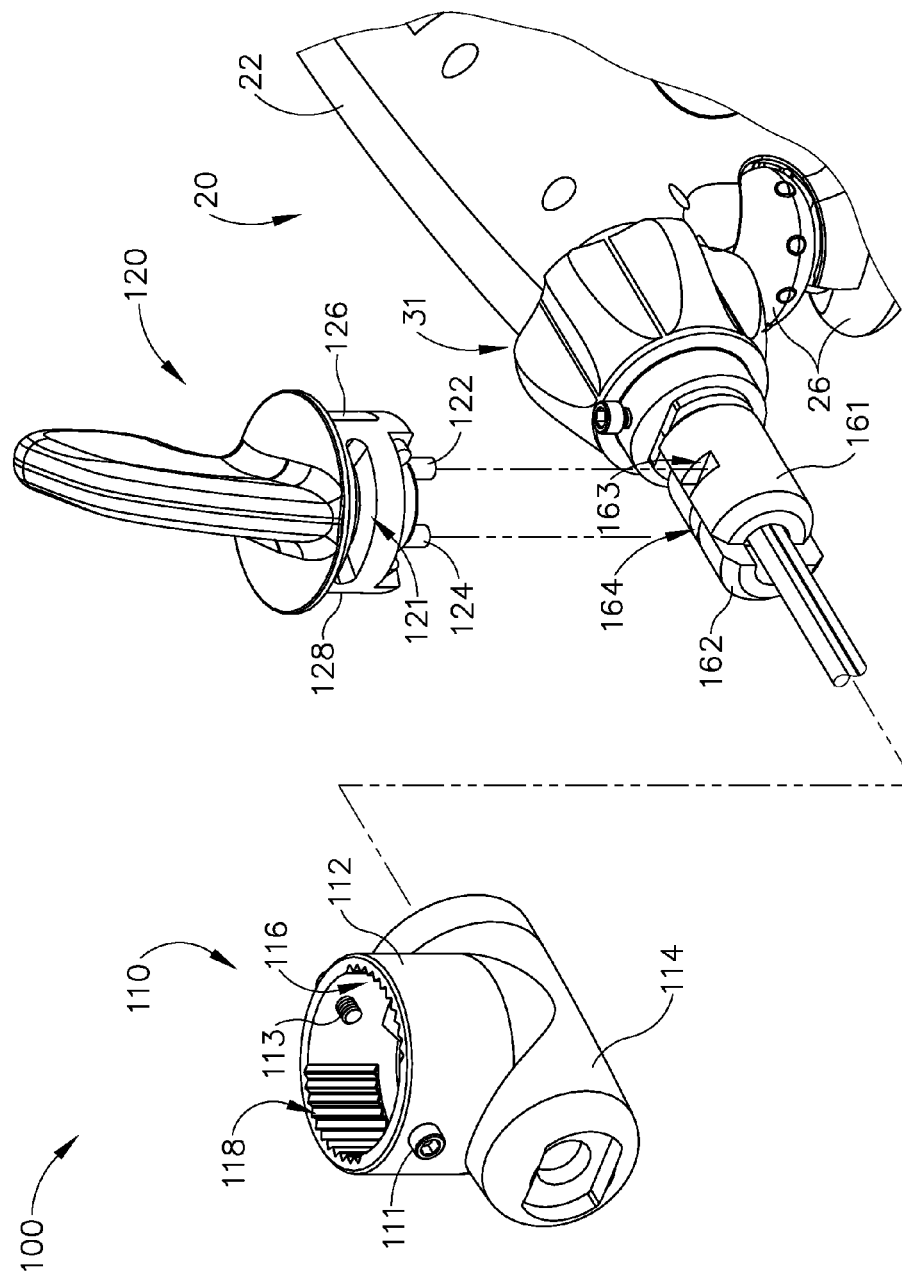
FIG. 9 depicts a partially exploded perspective view of an articulation control assembly of the instrument of FIG. 1.

As best seen in FIG. 9, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 164) formed in top surfaces of translatable members (161, 162). Channels (163, 164) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In some versions of instrument (10), articulation section (130) of shaft assembly (30) is operable to achieve articulation angles up to between approximately 15° and approximately 30°, both relative to the longitudinal axis of shaft assembly (30) when shaft assembly (30) is in a straight (non-articulated) configuration. Alternatively, articulation section (130) may be operable to achieve any other suitable articulation angles.

In some versions of instrument (10), narrowed section (164) of waveguide (180) has a thickness between approximately 0.01 inches and approximately 0.02 inches. Alternatively, narrowed section (164) may have any other suitable thickness. Also in some versions, narrowed section (164) has a length of between approximately 0.4 inches and approximately 0.65 inches. Alternatively, narrowed section (164) may have any other suitable length. It should also be understood that the transition regions of waveguide (180) leading into and out of narrowed section (164) may be quarter rounded, tapered, or have any other suitable configuration.

In some versions of instrument (10), flanges (136, 138) each have a length between approximately 0.1 inches and approximately 0.2 inches. Alternatively, flanges (136, 138) may have any other suitable length. It should also be understood that the length of flange (136) may differ from the length of flange (138). Also in some versions, flanges (136, 138) each have a diameter between approximately 0.175 inches and approximately 0.2 inches. Alternatively, flanges (136, 138) may have any other suitable outer diameter. It should also be understood that the outer diameter of flange (136) may differ from the outer diameter of flange (138).

While the foregoing exemplary dimensions are provided in the context of instrument (10) as described above, it should be understood that the same dimensions may be used in any of the other examples described herein. It should also be understood that the foregoing exemplary dimensions are merely optional. Any other suitable dimensions may be used.

II. Exemplary Alternative Features for Selectively Locking Articulation Section

In some versions of instrument (10) it may be desirable to provide features that are configured to selectively lock articulation section (130) at a selected state of articulation. For instance, when articulation section (130) is in a straight configuration, it may be desirable to lock articulation section (130) in the straight configuration in order to prevent inadvertent lateral deflection of end effector (40) at articulation section (130). Similarly, when articulation section (130) is bent to a selected articulation angle, it may be desirable to lock articulation section (130) at that selected articulation angle in order to prevent inadvertent lateral deflection of end effector (40) way from that selected articulation angle at articulation section (130). Various examples of features that are configured to selectively lock articulation section (130) at a selected state of articulation will be described in greater detail below. Other examples will be apparent to those of ordinary skill in the art according to the teachings herein.

A. Articulation Control Assembly with Resiliently Biased Locking Paddle on Knob

Figure 11:
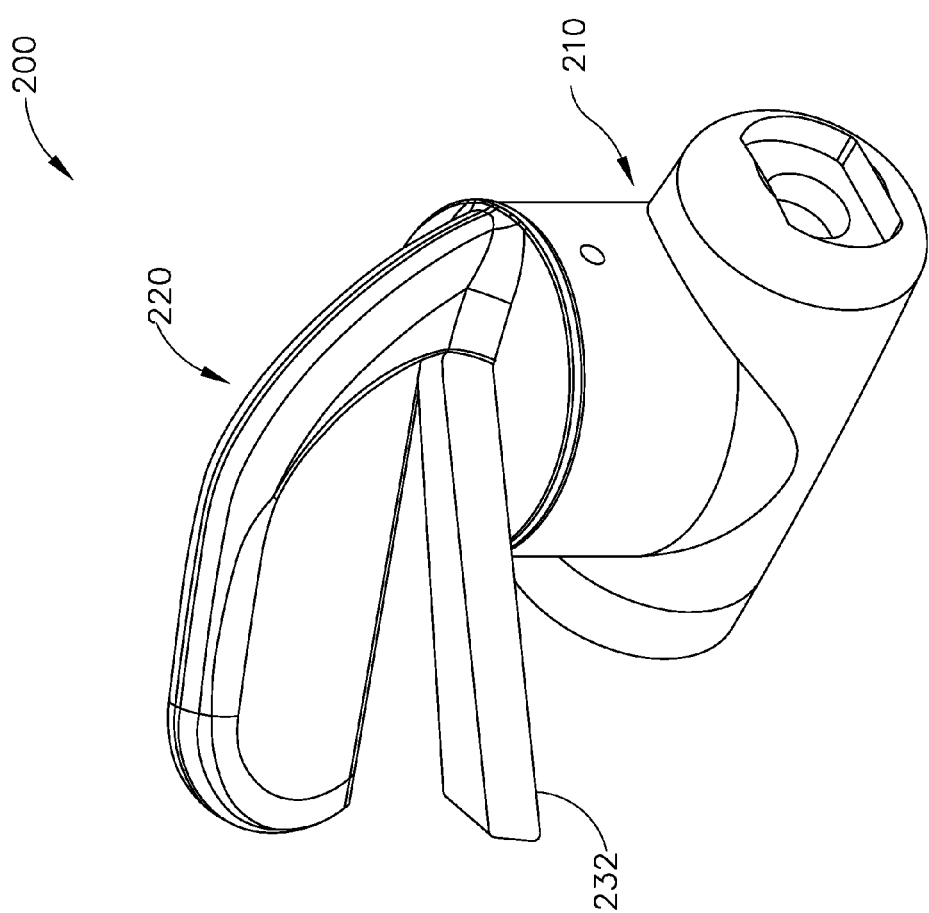
FIG. 11 shows a perspective view of an exemplary alternative articulation control assembly that may be incorporated into the instrument of FIG. 1, with a locking feature in a locked configuration.
Figure 12A:
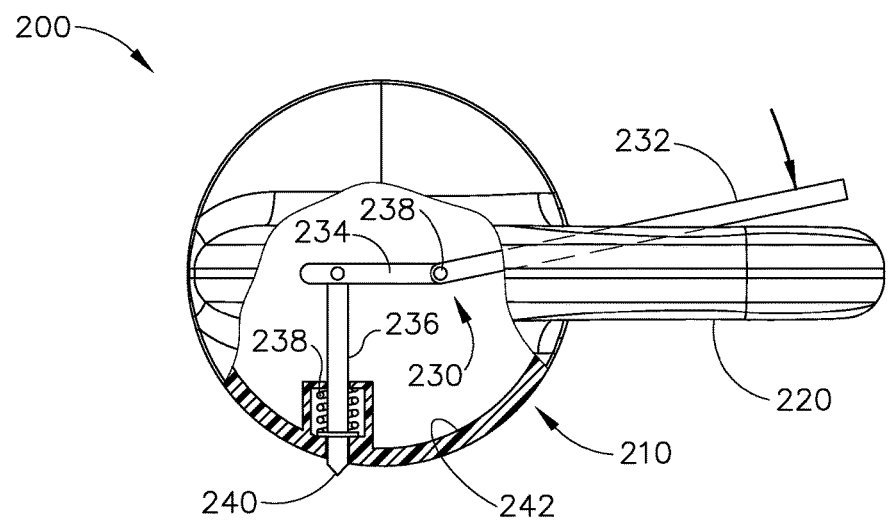
FIG. 12A depicts a top plan view of the articulation control assembly of FIG. 11, with the locking feature in the locked configuration.
Figure 12B:
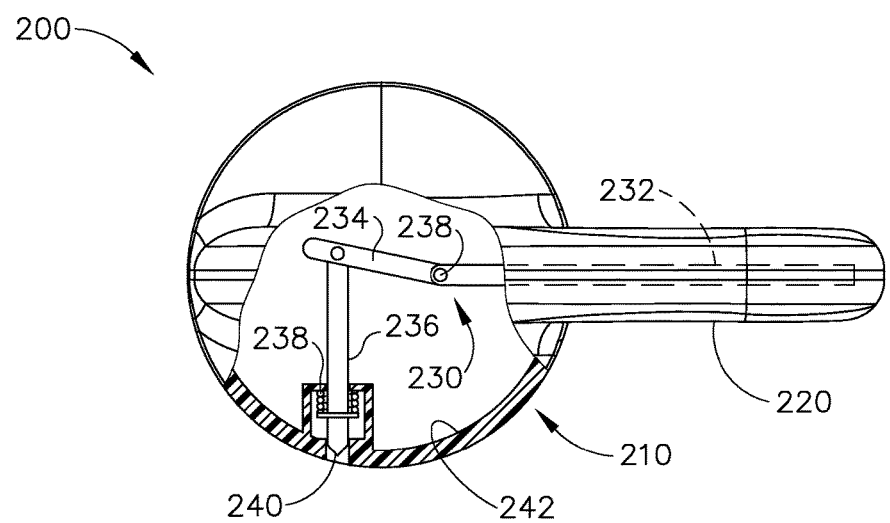
FIG. 12B depicts a top plan view of the articulation control assembly of FIG. 11, with the locking feature in an unlocked configuration.

FIGS. 11-12B show an exemplary articulation control assembly (200) that may be readily incorporated into instrument (10) in place of articulation control assembly (100). Except as otherwise described below, articulation control assembly (200) is configured and operable just like articulation control assembly (100) described above. Articulation control assembly (200) of this example comprises a housing (210) and a knob (220). Rotation of rotation knob (220) relative to housing (210) causes articulation of an articulation section of a shaft assembly, such as articulation section (130) of shaft assembly (30). Articulation control assembly (200) of this example further comprises a locking feature (230) that is configured to selectively prevent the rotation of knob (220). It should be understood that, by preventing rotation of knob (220), locking feature (230) further prevents articulation of the articulation section of the shaft assembly. Locking feature (230) may be used in lieu of, or in addition to, other features discussed herein that selectively prevent rotation of knob (220); and that selectively lock articulation section (130) in a particular deflected position relative to the longitudinal axis defined by outer sheath (32).

As shown in FIGS. 11-12B, locking feature (230) of the present example includes a paddle (232), a lever member (234), a lock arm (236), and a spring (238). In the present example, paddle (232) is operably coupled to lever member (234) at pivot point (238). Paddle (232) and lever member (234) together form an oblique angle at pivot point (238). Pivot point (238) provides a pivotal coupling of paddle (232) and lever member (234) to the underside of knob (220). Paddle (232) and lever member (234) are rigidly coupled together such that the pivoting of paddle (232) about pivot point (238) causes lever member (234) to rotate or pivot in the same direction about pivot point (238). In particular, paddle (232) and lever member (234) are pivotable between a first position (FIG. 12A) and a second position (FIG. 12B). In the first position, paddle (232) is oriented obliquely relative to a vertical plane (going into and out of the page in the views shown in FIGS. 12A-12B) that is defined by knob (220); while lever member (234) extends along the vertical plane defined by knob (220). In the second position, paddle (232) extends along the vertical plane defined by knob (220); while lever member (234) is oriented obliquely relative to the vertical plane defined by knob (220).

Lever member (234) is pivotably coupled to lock arm (236). Lock arm (236) is resiliently biased toward inner wall (242) housing (210) by spring (238). In the locked configuration (FIG. 12A), lock arm (236) positively engages housing (210) and thereby prevents rotation of knob (220) relative to housing (210). Lock arm (236) is configured to translate along a path that is transverse to the vertical plane defined by knob (220). In particular, lock arm (236) translates along this path in response to pivoting of paddle (232) and lever member (234) between the first and second positions as described above. By way of example only, the underside of knob (220) may include a channel that is sized to receive and guide lock arm (236) in order to keep lock arm (236) on this linear path of travel. As another merely illustrative example, one or more guiding features (e.g., rails, etc.), may be configured to receive and guide lock arm (236) in order to keep lock arm (236) on this linear path of travel.

In the example shown, lock arm (236) includes a pointed end (240) that is configured to frictionally engage an inner wall (242) of housing (210). In some examples, inner wall (242) of housing (210) includes one or more features to enhance the positive engagement between lock arm (236) and housing (210). For example, inner wall (242) of housing (210) may include notches, splines, detents, frictional coatings, frictional surface treatments, etc., with which the lock arm (236) may engage. It should also be understood that pointed end (240) may include an elastomeric material and/or any other suitable feature(s) to promote a locking relationship between pointed end (240) and inner wall (242) of housing (210).

When articulation control assembly (200) is in the configuration shown in FIG. 12A, articulation control assembly (200) is in a locked state due to engagement between pointed end (240) of lock arm (242) and inner wall (242) of housing (210). This locked state provides locking of the articulation state of the articulation section of the shaft assembly, regardless of whether the articulation section is in a straight configuration or a bent configuration. In order to unlock articulation control assembly (200) in order to change the articulation state of the articulation section, an operator may drive paddle (232) from the position shown in FIG. 12A to the position shown in FIG. 12B by pinching paddle (232) toward knob (220). This causes paddle (232) to pivot about pivot point (238) toward knob (220), which in turn causes pivoting of lever member (234) in the same angular direction about pivot point (238). This pivoting of lever member (234) pulls lock arm (236) away from inner wall (242) of housing (210), such that pointed end (240) disengages inner wall (242) of housing (210). With pointed end (240) disengaged from inner wall (242) of housing (210), articulation control assembly (200) is in an unlocked state, such that knob (220) may be rotated relative to housing (210) to change the articulation state of the articulation section of the shaft assembly.

Once the user has reached the desired articulation state, the operator may release paddle (232). When the operator releases paddle (232), the resilience of spring (238) may return lock arm (236), lever member (234), and paddle (232) back to the locked configuration (FIG. 12A). The articulation section will thus be re-locked at the adjusted articulation state.

B. Articulation Control Assembly with Upwardly Biased Clutching Lock

Figure 13A:
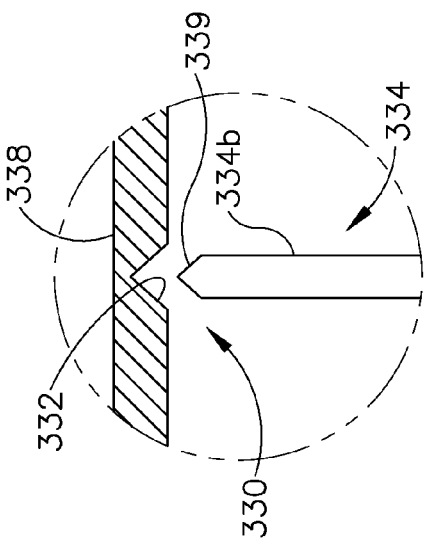
FIG. 13A depicts a detailed side elevational view of the locking feature of the articulation control assembly of FIG. 13 in the locked configuration, with a housing portion shown in cross-section.
Figure 13B:
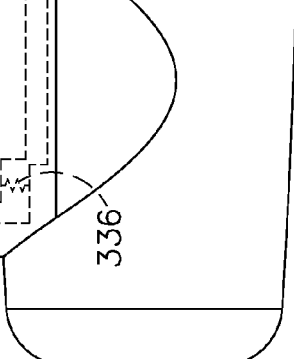
FIG. 13B depicts a detailed side elevational view of the locking feature of the articulation control assembly of FIG. 13 in the unlocked configuration, with a housing portion shown in cross-section.
Figure 13:
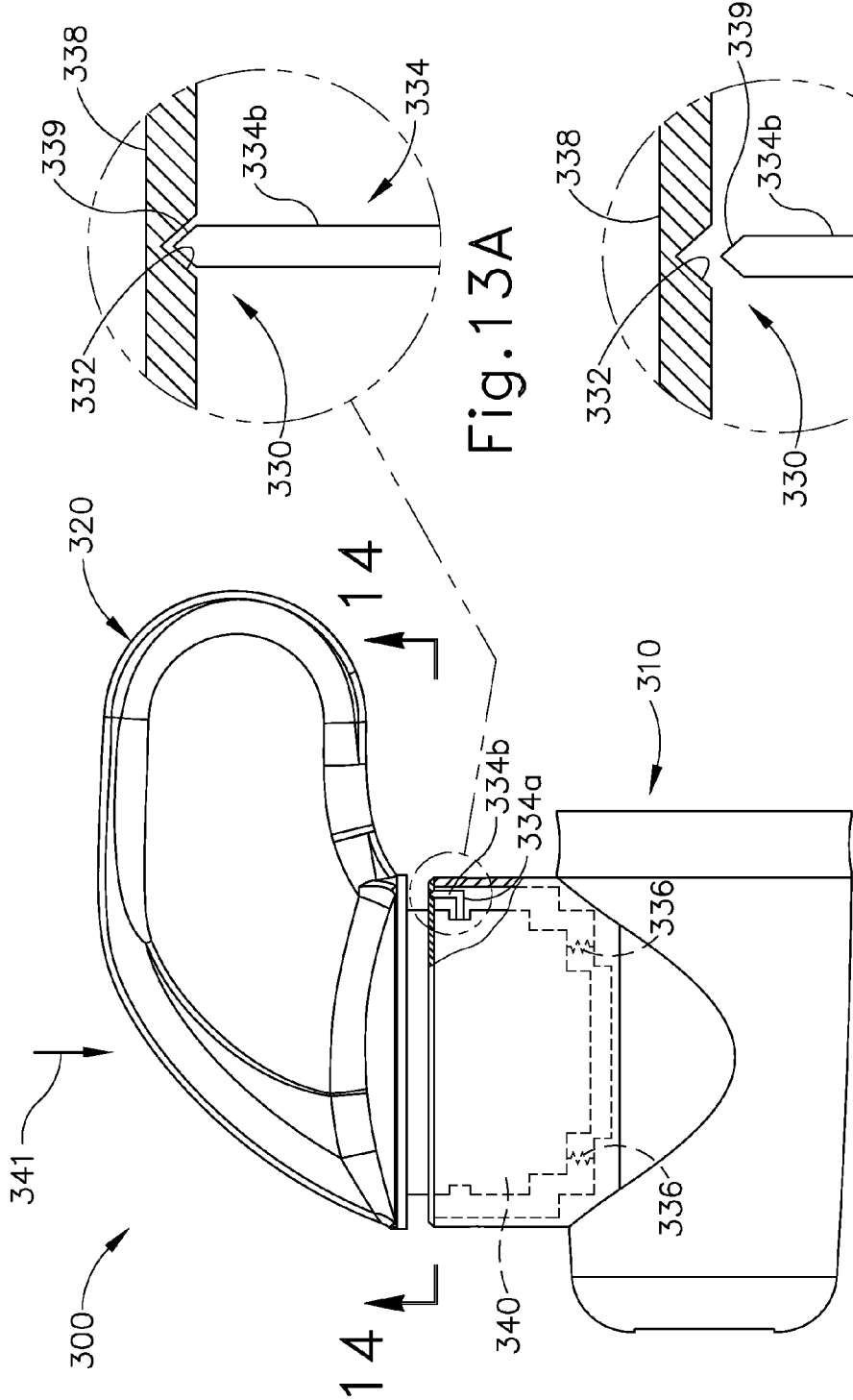
FIG. 13 depicts a side elevational view of another exemplary alternative articulation control assembly that may be incorporated into the instrument of FIG. 1, with a locking feature in a locked configuration.
Figure 14:
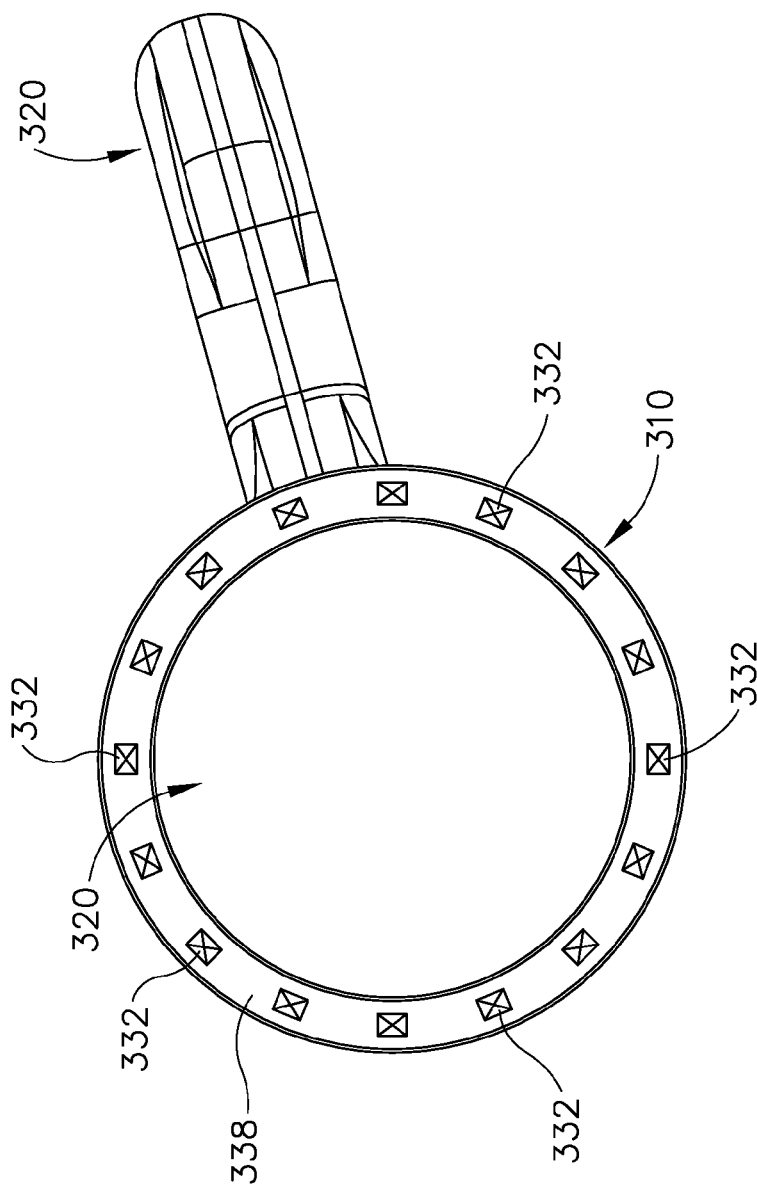
FIG. 14 depicts a bottom cross-sectional view of a knob of the articulation control assembly of FIG. 13, taken along line 14-14 of FIG. 13.

FIGS. 13-14 show another exemplary articulation control assembly (300) that may be readily incorporated into instrument (10) in place of articulation control assembly (100). Except as otherwise described below, articulation control assembly (300) is configured and operable just like articulation control assembly (100) described above. Articulation control assembly (300) of this example comprises a housing (310) and a knob (320). Rotation of rotation knob (320) relative to housing (310) causes articulation of an articulation section of a shaft assembly, such as articulation section (130) of shaft assembly (30). Articulation control assembly (300) of this example further comprises a locking feature (330) that is configured to selectively prevent the rotation of knob (320). It should be understood that, by preventing rotation of knob (320), locking feature (330) further prevents articulation of the articulation section of the shaft assembly. Locking feature (330) may be used in lieu of, or in addition to, other features discussed herein that selectively prevent rotation of knob (320); and that selectively lock articulation section (130) in a particular deflected position relative to the longitudinal axis defined by outer sheath (32).

As shown in FIGS. 13-13B, locking feature (330) of the present example includes a plurality of female spline features (332) disposed on housing (310), and a male spline feature (334) coupled to knob (320). Female spline features (332) are more particularly defined as recesses disposed circumferentially and presented downwardly along an annular lip (338) (FIG. 14) that surrounds a body portion (340) of knob (320) (when knob is received within housing (310)). Male spline feature (334) includes a first portion (334a) that extends radially outwardly from body portion (340) and a second portion (334b) that extends upwardly, perpendicular to the first portion (334b). While only one male spline feature (334) is shown, it should be understood that body portion (340) may include two more male spline features (334). For instance, a plurality of male spline features (334) may be angularly spaced along at least a portion of the perimeter of body portion (340). It should also be understood that female spline features (332) may be angularly spaced along any suitable angular range along the circumference of annular lip (338).

As shown, female and male spline members (334, 332) are similarly shaped such that the female spline members (332) are defined as cavities having shapes that complement the end (339) of the male spline feature (334). FIG. 13A shows male spline feature (334) received in female spline feature (332). In this state, locking feature (330) prevents knob (320) from rotating relative to housing (310), thereby locking articulation section (130) in its current articulated (or non-articulated) position relative to the longitudinal axis defined by outer sheath (32). In the present example, female spline feature (332) and end (339) of male spline features (334) define pyramidal shapes with pointed portions. In some other examples, spline features (332, 334) are substituted with a plurality of complementary teeth arranged in a starburst pattern. Various suitable other ways in which spline features (332, 334) may be may be configured will be apparent to those of ordinary skill in the art in view of the teachings herein.

In the present example, a resilient element (336) biases knob (320) upwardly into a position where an end (339) of male spline feature (334) is received with and engages one of the female spline features (332), thereby preventing the rotation of knob (320) relative to housing (310). Resilient element (336) may comprise a coil spring, a wave spring, a leaf spring, and/or any other suitable kind of resilient feature. In some examples, locking feature (330) may be configured to act as a slipping clutch mechanism. That is, in some such examples, the engagement of male spline feature (334) with one of the female spline features (332) may be overcome by a user applying sufficient rotational force to knob (320); but absent such force, the engagement will suffice to maintain the straight or articulated configuration of articulation section (130). It should therefore be understood that the ability to selectively lock knob (320) in a particular rotational position will provide selective locking of articulation section (130) in a particular deflected position relative to the longitudinal axis defined by outer sheath (32).

In some other examples, the male spline feature (334) and female spline features (332) are configured such that that it is difficult to overcome that engagement between male spline feature (334) and female spline features (332) by simply providing a rotational force to knob (320); or such that the rotational force required to overcome the engagement may cause unintended damage to one or more components of the instrument (10). Such a configuration, where a relatively higher rotational force is required to rotate knob (320), may be provided for the prevention of unintended articulation as a result of inadvertent rotation of knob (320).

In the example shown, in order to enable rotation of knob (320), the operator must press knob (320) in a direction (defined by arrow (341)), along an axis that is perpendicular to the longitudinal axis of shaft assembly (30). In the present example, knob (320) is pressed along the same axis about which knob (320) is rotated in order to drive articulation of articulation section (130). When the user depresses knob (320) with a sufficient force to overcome the bias of a resilient element (336), end (339) of male spline feature (334) disengages from female spline feature (332) as shown in FIG. 13B. Knob (320) is then free to rotate relative to housing (310) as the operator continues to press downwardly on knob (320). In examples where the engagement between male spline feature (334) and female spline features (332) may be overcome by applying sufficient rotational disengagement force to knob (320), the rotational force required to rotate the knob (320) in the unlocked configuration is less than the rotational force required to disengage male spline feature (334) from female spline feature (332).

When the operator rotates knob (320) while knob (320) is in the downward, unlocked position, such rotation of knob (320) causes the articulation of articulation section (130). Once the user has articulated articulation section (130) a desired amount (whether to or from an articulated state), the user may release the downward force (in the direction of arrow (341)) on knob (320). Resilient element (336) will then resiliently urge knob (320) back to the locked configuration of FIGS. 13 and 13A, such that articulation section (130) is locked in the adjusted articulation state relative to the longitudinal axis defined by outer sheath (32). In some examples, the operator may need to ensure the proper alignment of corresponding male spline feature (334) and a particular female spline feature (332) to enable the knob (320) to return to the locked configuration. However, in some examples, locking feature (330) may be configured to circumferentially align corresponding male spline feature (334) with a circumferentially adjacent female spline feature (332) to ensure a smooth transition to the locked configuration. In other words, spline features (332, 334) may be configured to self-align with each other. Various suitable ways in which locking feature (330) may be may be configured will be apparent to those of ordinary skill in the art in view of the teachings herein.

C. Articulation Control Assembly with Downwardly Biased Clutching Lock

FIGS. 15A-17 show another exemplary articulation control assembly (400) that may be readily incorporated into instrument (10) in place of articulation control assembly (100). Except as otherwise described below, articulation control assembly (400) is configured and operable just like articulation control assembly (100) described above. Articulation control assembly (400) of this example comprises a housing (410) and a knob (420). Rotation of rotation knob (420) relative to housing (410) causes articulation of an articulation section of a shaft assembly, such as articulation section (130) of shaft assembly (30). Articulation control assembly (400) of this example further comprises a locking feature (430) that is configured to selectively prevent the rotation of knob (420). It should be understood that, by preventing rotation of knob (420), locking feature (430) further prevents articulation of the articulation section of the shaft assembly. Locking feature (430) may be used in lieu of, or in addition to, other features discussed herein that selectively prevent rotation of knob (420); and that selectively lock articulation section (130) in a particular deflected position relative to the longitudinal axis defined by outer sheath (32). Locking feature (430) is shown in a locked configuration in FIG. 15A and an unlocked configuration in FIG. 15B.

Figure 15A:
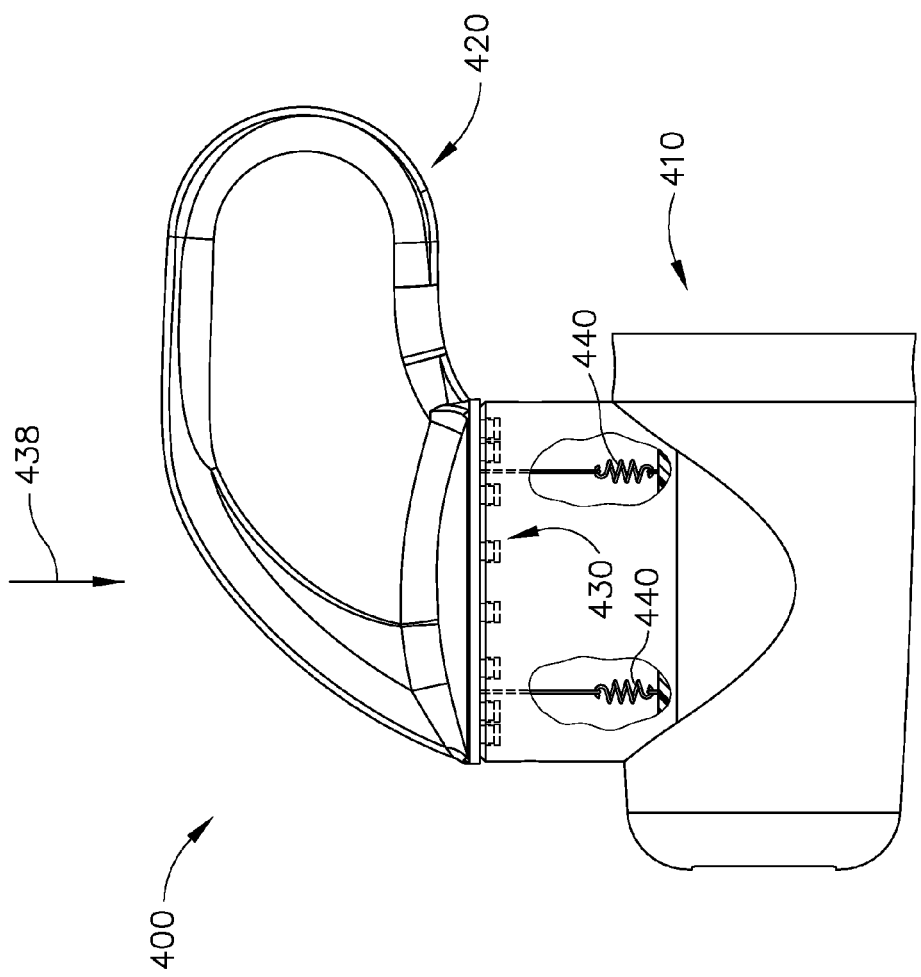
FIG. 15A depicts a side elevational view of yet another exemplary alternative articulation control assembly that may be incorporated into the instrument of FIG. 1, with a locking feature in a locked configuration.
Figure 15B:
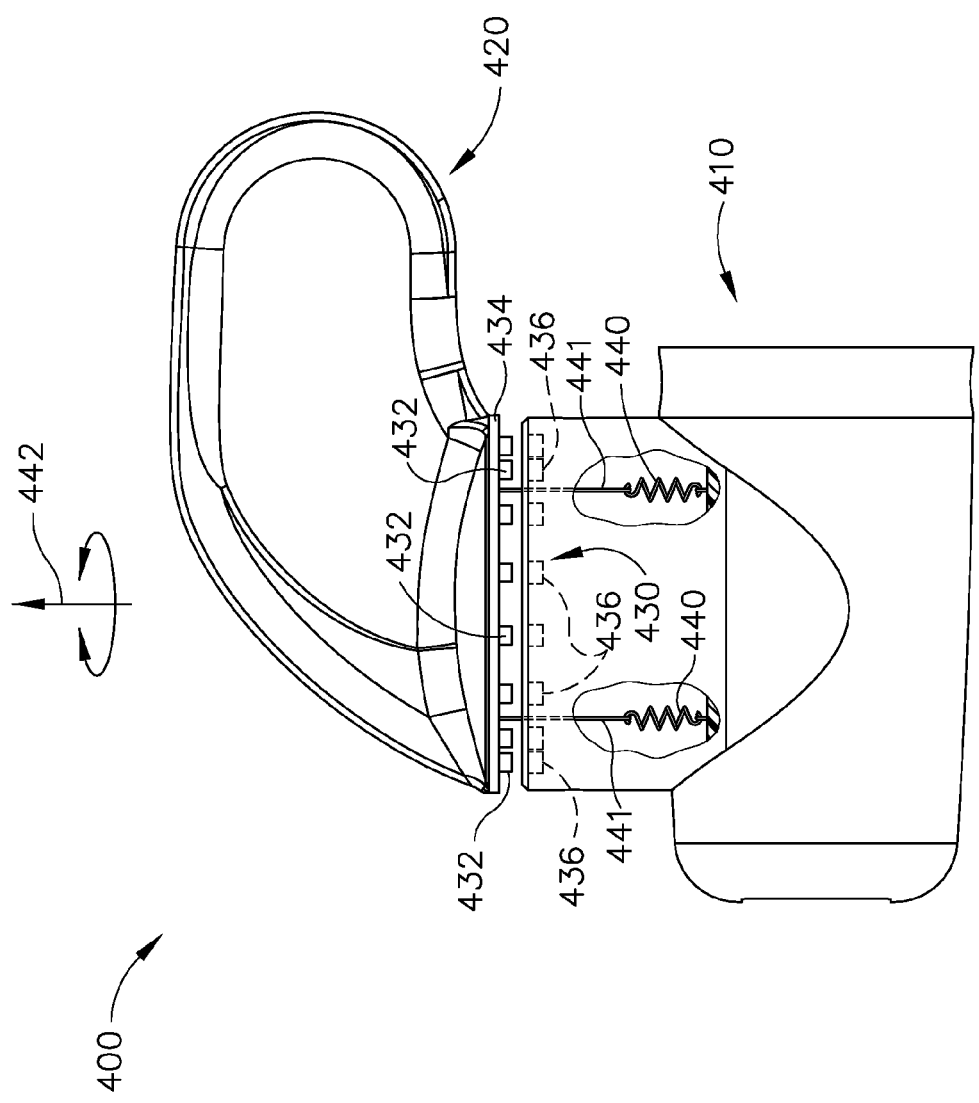
FIG. 15B depicts a side elevational view of the articulation control assembly of FIG. 15A, with the locking feature in an unlocked configuration.

Locking feature (430) of the present example comprises a plurality of male spline features (432) and a plurality of female spline features (436). As best seen in FIG. 15B, male spline features (432) extend downwardly (direction defined by defined by arrow (438)) from lip (434) of knob (420). As best seen in FIG. 16, male spline features (432) are angularly spaced in an annular array along the underside of lip (434). Male spline features (432) of the present example are generally rectangular in shape. Alternatively, male spline features (432) may instead have a pyramidal shape, a starburst configuration, and/or any other suitable configuration.

Figure 17:
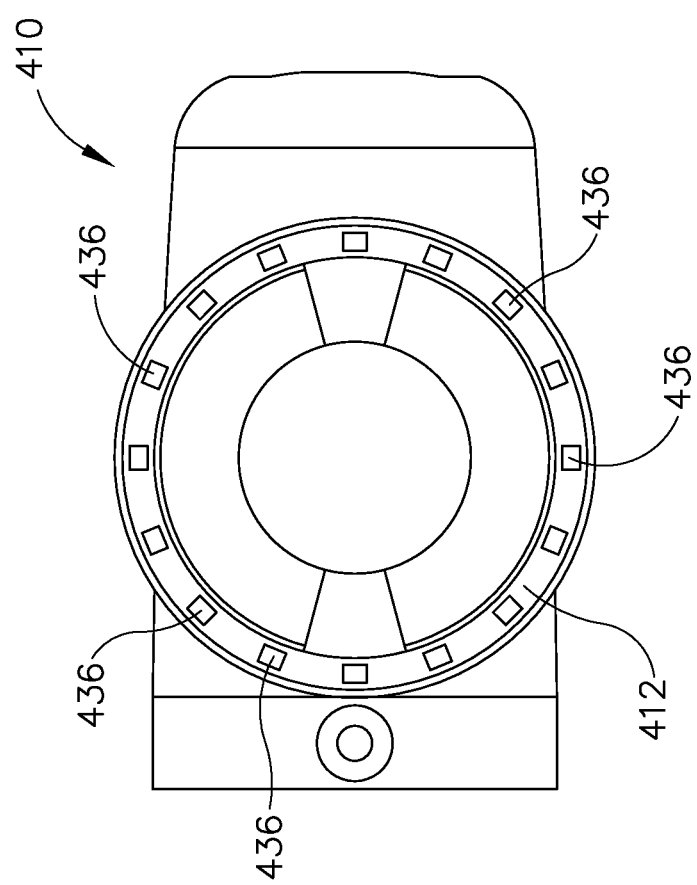
FIG. 17 depicts a top plan view of a housing of the articulation control assembly of FIG. 15A.

As best seen in FIG. 15B, female spline features (436) comprise recesses that are formed in an upwardly facing surface (412) of housing (410). As best seen in FIG. 17, female spline features (436) are angularly spaced in an annular array along upwardly facing surface (412) with spacing that complements the spacing of male spline features (432). Female spline features (436) are shaped similarly to male spline features (432) such that female spline features (436) define generally rectangular recesses, and are spaced apart from one another circumferentially such that female spline features (436) may receive correspondingly shaped and angularly spaced male spline features (432) as shown in FIG. 15A. In the present example, there are an equal number of male and female spline features (432, 436). However, in other examples, there may be fewer male spline features (432) than female spline features (436), provided that the male spline features (432) are configured to be received in corresponding female spline features (436) (e.g., proper sizing and angular spacing). When male spline features (432) are positioned in female spline features (436), the engagement between spline features (432, 436) prevents knob (420) from rotating relative to housing (410). Thus, when locking feature (430) is in a locked state due to engagement between spline features (432, 436), locking feature (430) locks the articulation section at its current state of articulation relative to the longitudinal axis of the shaft assembly.

In the present example, a pair of coil springs (440) is operably coupled to knob (420) via a pair of links (441) that resiliently bias knob (420) downwardly (in the direction defined by arrow (438)). Springs (440) thus bias knob (420) and male spline features (432) into the locked position shown in FIG. 15A. Due to the engagement between male and female spline features (432, 436), knob (420) is unable to rotate relative to housing (410). Of course, any other suitable kind of resilient member(s) may be used in addition to or in lieu of coil springs (440).

In some examples, locking feature (430) may be configured to act as a slipping clutch mechanism such that a sufficient amount of angular force on knob (420) causes male spline features (432) to slip between female spline features (436). In some such examples, male and/or female spline features (432, 436) may include ramped or cammed surfaces to enable the slipping clutch action therebetween. In some such examples, the engagement of male spline features (432) with one of the female spline features (436) may be overcome by a user applying sufficient rotational force to knob (420); but absent such force, the engagement will suffice to maintain the straight or articulated configuration of articulation section (130). It should therefore be understood that the ability to selectively lock knob (420) in a particular rotational position lock will enable an operator to selectively lock articulation section (130) in a particular deflected position relative to the longitudinal axis defined by outer sheath (32).

In the example shown, in order to enable rotation of knob (420), the operator must pull knob (420) in the direction of arrow (442) along an axis that is perpendicular to the longitudinal axis of shaft assembly (30), into the unlocked configuration shown in FIG. 15B. In the present example, knob (420) is pulled along the same axis about which knob (420) is rotated in order to drive articulation of articulation section (130). As shown, in the unlocked configuration, male spline features (432) are disengaged from female spline features (436) (i.e., male spline features (432) are spaced from female spline features (436)). Thus, in the unlocked configuration, knob (420) is able to rotate relative to housing (410) along an axis that is perpendicular to the longitudinal axis of outer sheath (32) and cause articulation of articulation section (130), for example. In examples where the engagement between male spline features (432) and female spline features (436) may be overcome by applying sufficient rotational disengagement force to knob (420), the rotational force required to rotate the knob (420) in the unlocked configuration is less than the rotational force required to disengage male spline features (432) from female spline features (436).

When the operator rotates knob (420) while knob (420) is in the upward, unlocked position, such rotation of knob (420) causes the articulation of articulation section (130). Once the user has articulated articulation section (130) a desired amount (whether to or from an articulated state), the user may release the upward force on knob (420). Springs (440) will then resiliently urge knob (420) back to the locked configuration of FIG. 15A, such that articulation section (130) is locked in the adjusted articulation state relative to the longitudinal axis defined by outer sheath (32). In some examples, the operator may need to ensure the proper alignment of male spline features (432) with female spline features (436) to enable the knob (420) to return to the locked configuration. However, in some examples, locking feature (430) may be configured to circumferentially align male spline features (432) with circumferentially adjacent female spline features (332) to ensure a smooth transition to the locked configuration. In other words, spline features (432, 436) may be configured to self-align with each other. Various suitable ways in which locking feature (430) may be may be configured will be apparent to those of ordinary skill in the art in view of the teachings herein.

D. Articulation Control Assembly with Button Actuated Locking Feature

Figure 18:
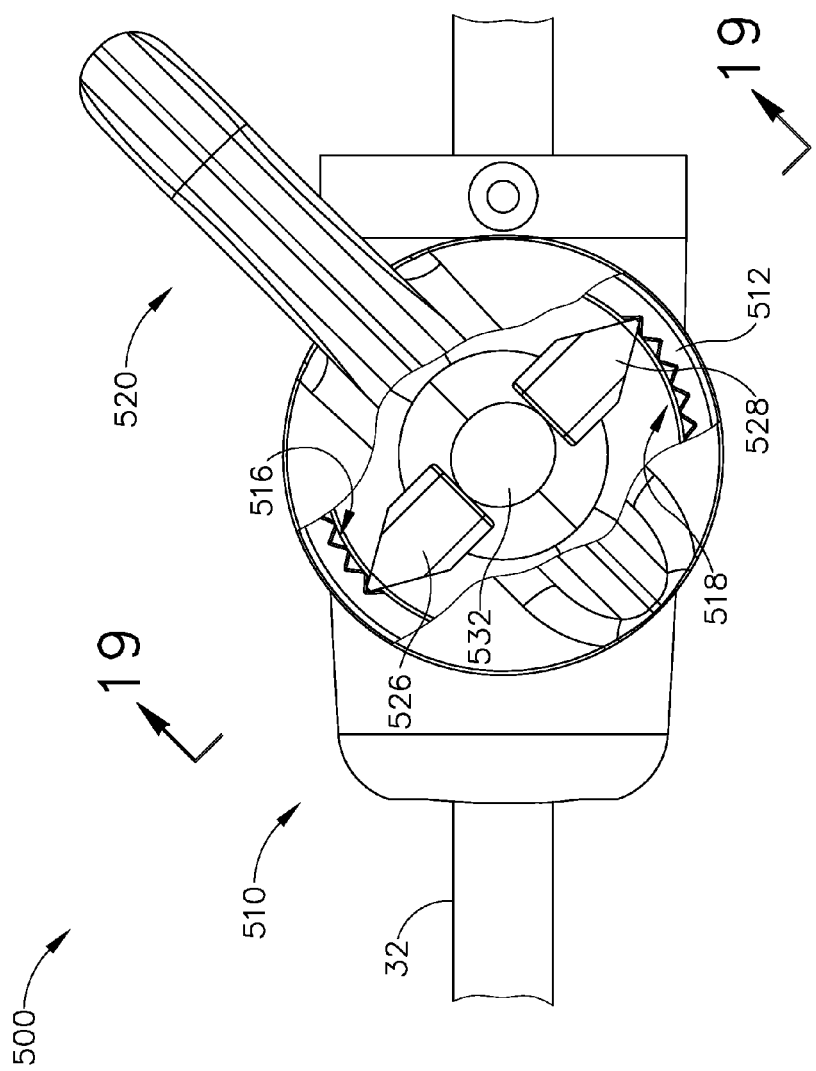
FIG. 18 depicts a top elevational view of yet another exemplary alternative articulation control assembly that may be incorporated into the instrument of FIG. 1, with a locking feature in a locked configuration.
Figure 19A:
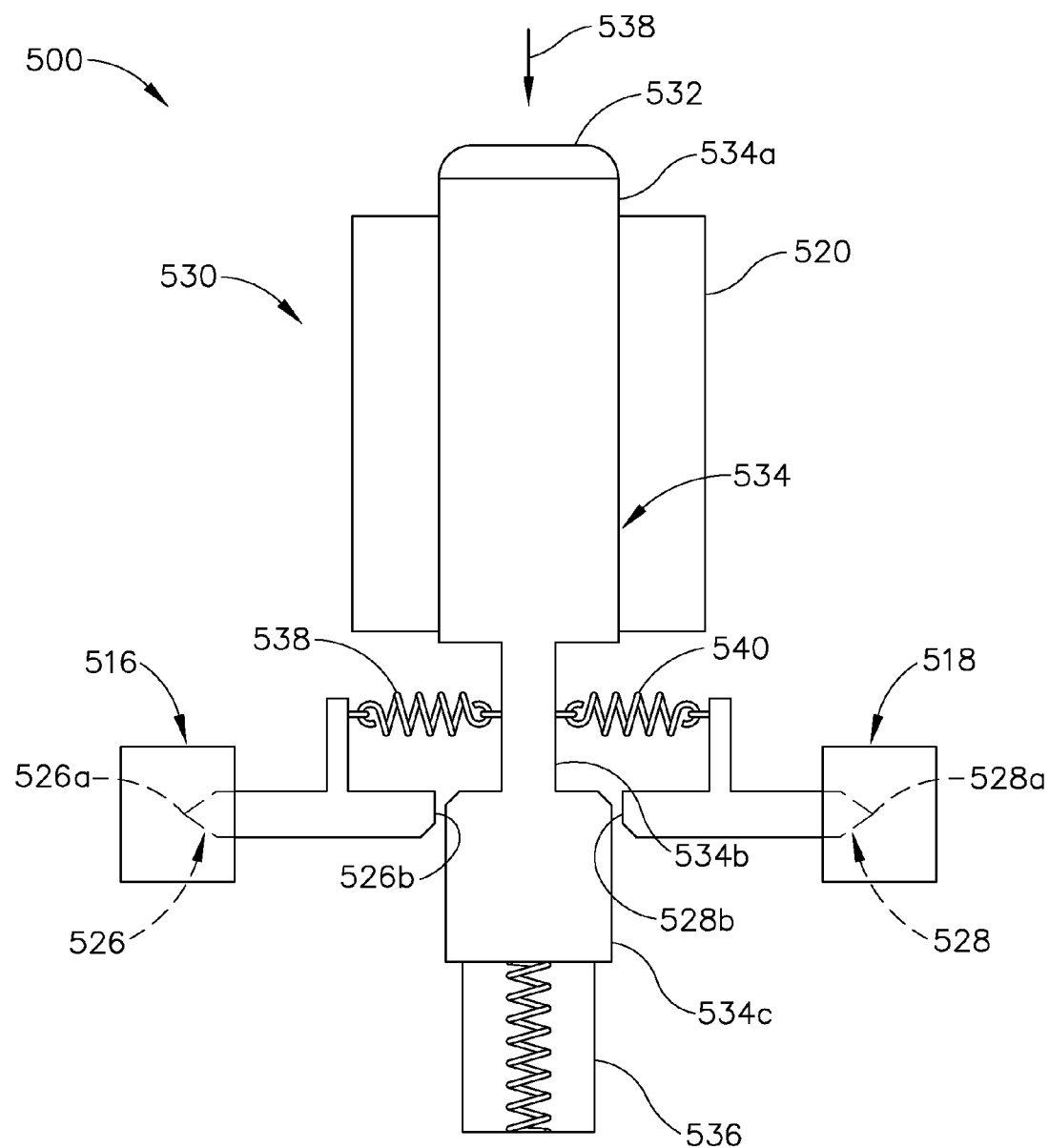
FIG. 19A depicts a partial, side cross-sectional view of the articulation control assembly of FIG. 18, with the locking feature in a locked configuration, taken along line 19-19 of FIG. 18.
Figure 19B:
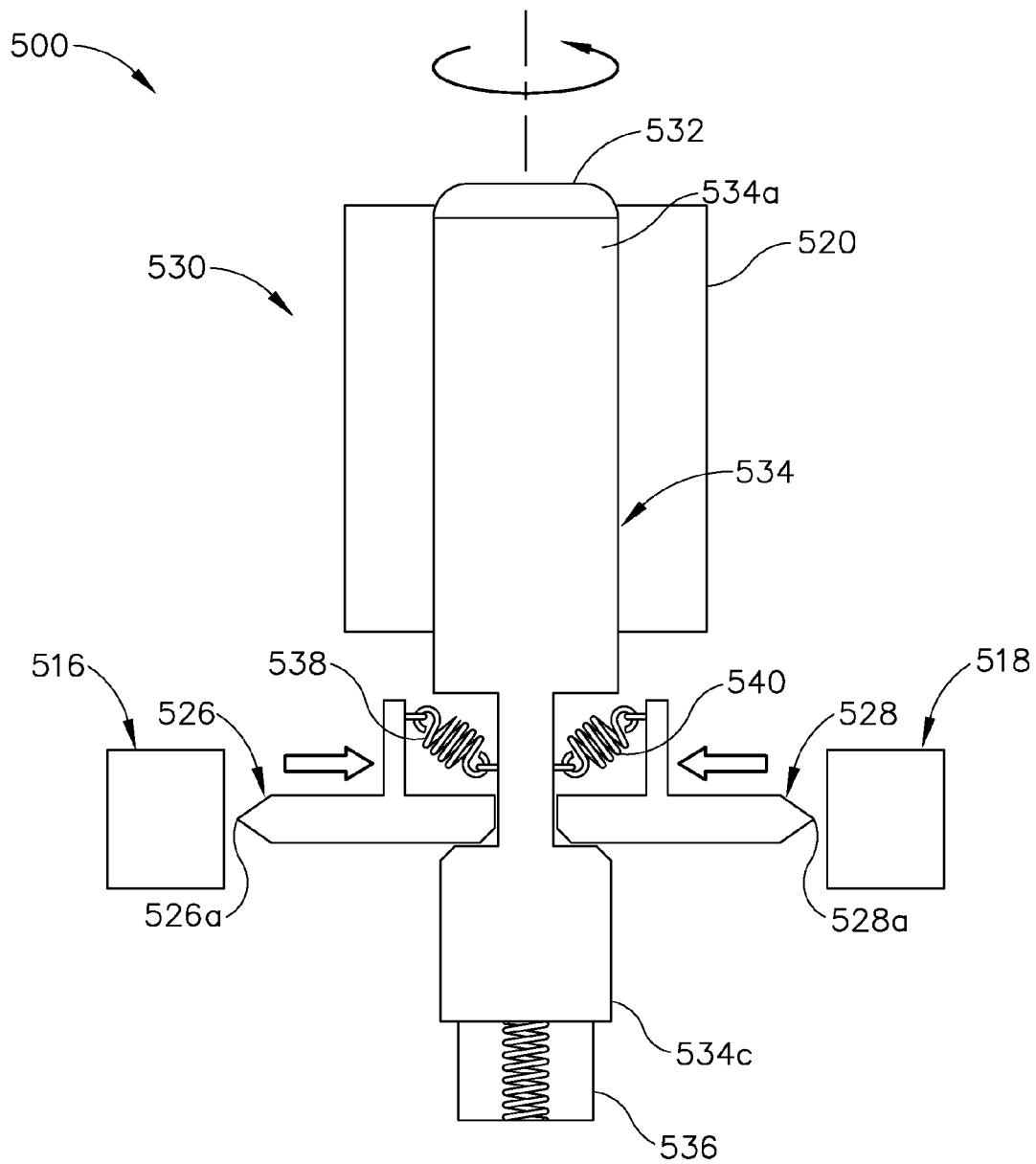
FIG. 19B depicts a partial, side cross-sectional view of the articulation control assembly of FIG. 18, with the locking feature in an unlocked configuration, taken along line 19-19 of FIG. 18.

FIGS. 18-19B show another exemplary articulation control assembly (500) that may be readily incorporated into instrument (10) in place of articulation control assembly (100). Except as otherwise described below, articulation control assembly (500) is configured and operable just like articulation control assembly (100) described above. Articulation control assembly (500) of this example comprises a housing (510) and a knob (520). Rotation of rotation knob (520) relative to housing (510) causes articulation of an articulation section of a shaft assembly, such as articulation section (130) of shaft assembly (30). Articulation control assembly (500) of this example further comprises a locking feature (530) that is configured to selectively prevent the rotation of knob (520). It should be understood that, by preventing rotation of knob (520), locking feature (530) further prevents articulation of the articulation section of the shaft assembly. Locking feature (530) may be used in lieu of, or in addition to, other features discussed herein that selectively prevent rotation of knob (520); and that selectively lock articulation section (130) in a particular deflected position relative to the longitudinal axis defined by outer sheath (32).

In the present example, locking feature (530) comprises a button (532) that is operably coupled to a shaft (534). Shaft (534) is slidably received in knob (520) along the same axis about which knob (520) rotates relative to housing (510). Shaft (534) has a first portion (534a), a second portion (534b), and a third portion (534c). Button (532) is positioned on top of first portion (534a) and is configured to protrude above the upper surface of knob (520) to enable an operator to readily depress button (532) as described below. As shown, first portion (534a) of shaft (534) and button (532) are shown to be separate components, but in other examples, button (532) may be unitarily formed with shaft (534). As shown, second portion (534b) of shaft (534) includes a smaller cross-sectional dimension (e.g., diameter) than the first and second portions (534a, 534c). Locking feature (430) further comprises a resilient feature (536), which in the present example is shown as a coil spring, but in other examples may be other types of resilient features. Resilient feature (536) biases shaft (534) upwardly into the position shown in FIG. 19A, whereby locking feature (530) is in a locked configuration.

In the present example, locking feature (530) further comprises a pair of outwardly extending engagement members (526, 528) including pointed ends (526a, 528a). Housing (510) includes a first cylindrical portion (512) that has inwardly presented teeth (516, 518). Teeth (516, 518) are configured to complement engagement members (526, 528). In particular, engagement members (526, 528) are configured to engage teeth (516, 518) in a detent relationship to thereby selectively lock the rotational position of knob (520) relative to housing (510). Engagement members (526, 528) and teeth (516, 518) are configured to operate substantially similar to engagement members (126, 128) with teeth (116, 118) as described above. However, in the present example, engagement members (526, 528) are retractable radially inwardly to disengage teeth (516, 518). A set of resilient members (538, 540) bias engagement members (526, 528) inwardly. Shaft (534) selectively resists this inward bias of engagement members (526, 528), depending on whether third portion (534c) is positioned on the same lateral plane as engagement members (526, 528) or second portion (534b) is positioned on the same lateral plane as engagement members (526, 528).

Shaft (534) translates along a vertical axis to selectively position portions (534b, 534c) on the same lateral plane as engagement members (526, 528) in response to depression and release of button (532). In particular, when button (532) is not being depressed, shaft (534) is in an upper, home position as shown in FIG. 19A due to the bias of resilient feature (536). In this state, third portion (534c) of shaft (534) is positioned on the same lateral plane as engagement members (526, 528). Due to the relatively larger size of the diameter of third portion (534c), third portion (534c) holds engagement members (526, 528) in an outward position, such that pointed ends (526a, 528a) are engaged with teeth (516, 518). This engagement between pointed ends (526a, 528a) and teeth (516, 518) prevents knob (520) from rotating relative to housing (510), thereby preventing articulation section (130) from articulating relative to the rest of shaft assembly (30). Thus, articulation section (130) is locked at its current state of articulation when locking feature (430) is in the state shown in FIG. 19A.

In order to unlock knob (520), and thereby unlock articulation section (130), the operator may press button (532) downwardly (in the direction of arrow (538)). When button (532) is depressed downwardly, shaft (534) overcomes the bias of resilient feature (536) and shaft (534) moves downwardly. As shaft (534) moves downwardly, radially inward portions (526b, 528b) of engagement features (526, 528) ride along third portion (534c) and engagement features (526, 528) are eventually urged inwardly by resilient members (538, 540) as radially inward portions (526b, 528b) become coincident with second portion (534b) of shaft (534), which has a smaller diameter than third portion (534c) of shaft (534). As engagement features (526, 528) move inwardly as shown in FIG. 19B, pointed ends (526a, 528a) of engagement features disengage from teeth (516, 518), respectively, and knob (520) is free to rotate relative to housing (510). The operator may thus rotate knob (520) while holding button (532) in the depressed state in order to adjust the articulation state of articulation section (130).

Once the operator has adjusted the articulation state of articulation section (130) to a desired amount (whether to or from an articulated state), the operator releases button (532). When the operator releases button (532), resilient feature (536) urges button (532) and shaft (534) upwardly (in a direction opposite to arrow (538)). As shaft (534) travels upwardly, third portion (534c) of shaft (534) eventually engages radially inward portions (526b, 528b) of engagement features (526, 528), thereby driving engagement features (526, 528) outwardly back to the positions shown in FIG. 19A. Engagement features (526, 528) thus re-engage teeth (516, 518) respectively, thereby re-locking the rotational position of knob (520) relative to housing (510), and further thereby locking the adjusted articulation state of articulation section (130). While shaft (534) is shown as providing a stepped transition between portions (534b, 534c), it should be understood that shaft (534) may instead provide a tapered transition between portions (534b, 534c). Radially inner portions (526b, 528b) of engagement members (526, 528) may slidably cam along such a tapered transition portion during the transition between the locked configuration (FIGS. 18, 19A) and unlocked configuration (FIG. 19B). Various other suitable ways in which locking feature (430) may be may be configured will be apparent to those of ordinary skill in the art in view of the teachings herein.

E. Articulation Control Assembly with Biased and Keyed Locking Feature

FIGS. 20-25 show another exemplary articulation control assembly (600) that may be readily incorporated into instrument (10) in place of articulation control assembly (100). Except as otherwise described below, articulation control assembly (600) is configured and operable just like articulation control assembly (100) described above. Articulation control assembly (600) of this example comprises a housing (610) and a knob (620). Rotation of rotation knob (620) relative to housing (610) causes articulation of an articulation section of a shaft assembly, such as articulation section (130) of shaft assembly (30). Articulation control assembly (600) of this example further comprises a locking feature (630) that is configured to selectively prevent the rotation of knob (620). It should be understood that, by preventing rotation of knob (620), locking feature (630) further prevents articulation of the articulation section of the shaft assembly. Locking feature (630) may be used in lieu of, or in addition to, other features discussed herein that selectively prevent rotation of knob (620); and that selectively lock articulation section (130) in a particular deflected position relative to the longitudinal axis defined by outer sheath (32).

Figure 20:
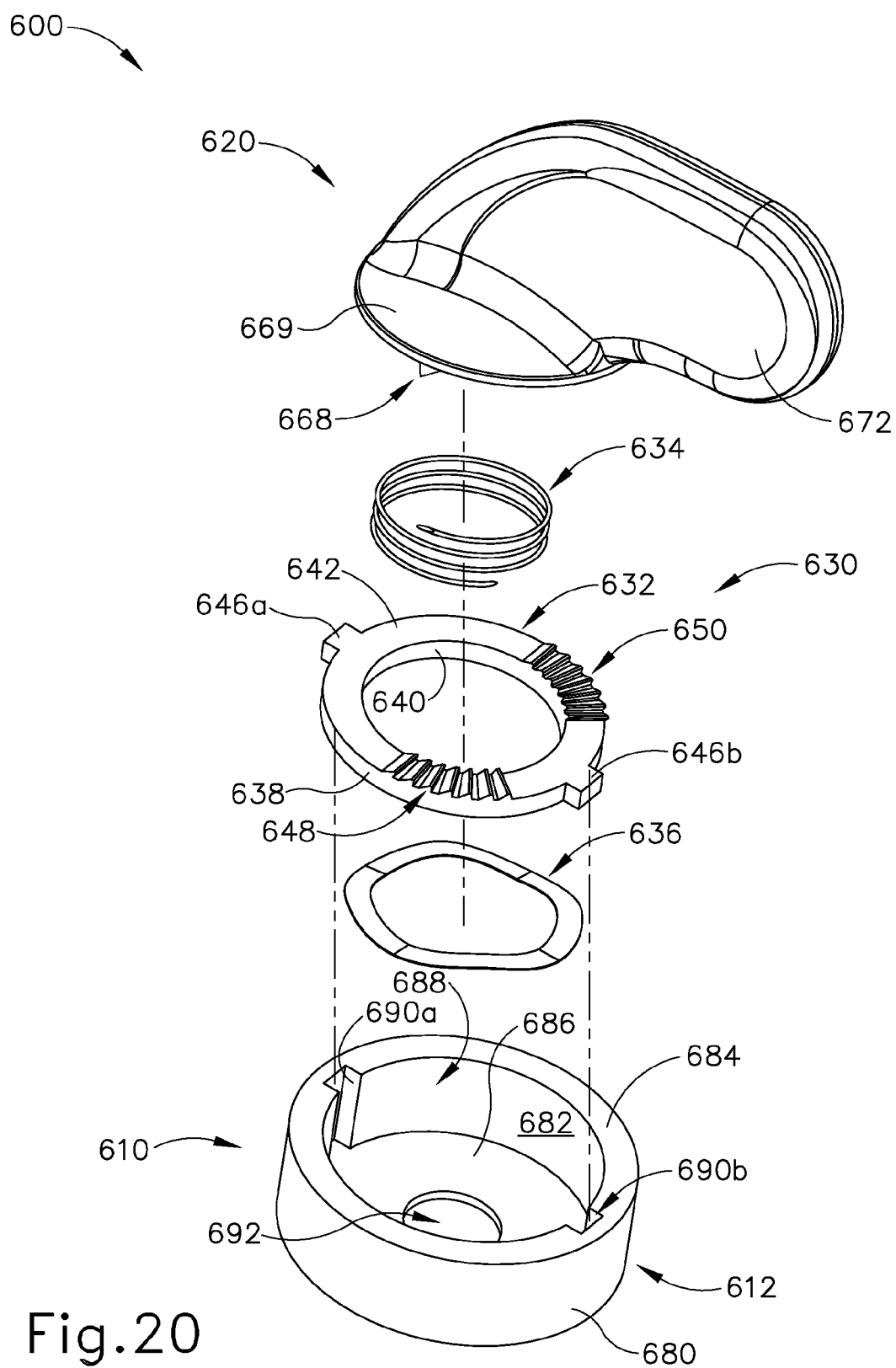
FIG. 20 depicts an exploded perspective view of another exemplary alternative articulation control assembly that may be incorporated into the instrument of FIG. 1.
Figure 24A:
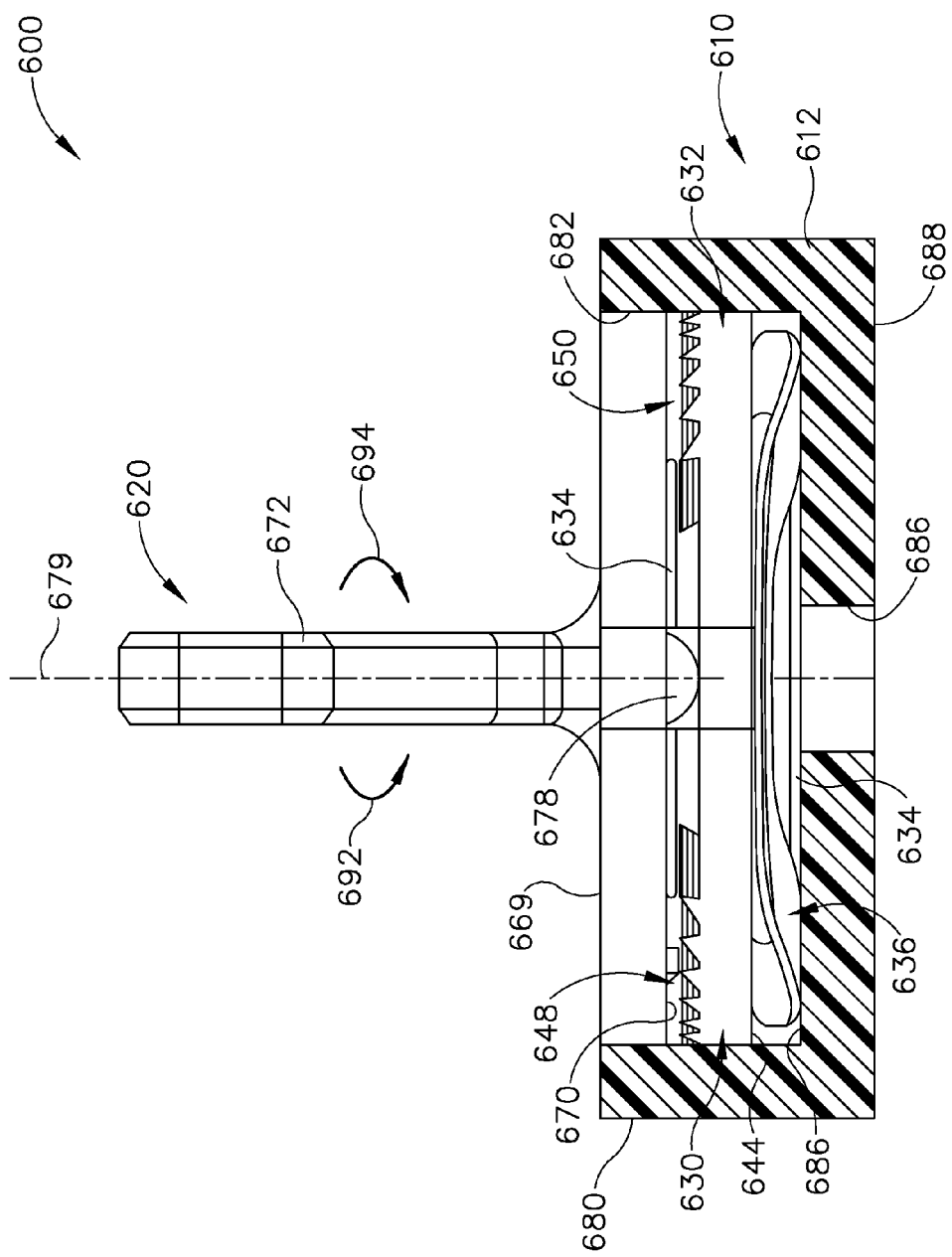
FIG. 24A shows a rear elevational view of the articulation control assembly of FIG. 20, with a portion of the housing hidden to show details of the components, and with the knob in a home position.
Figure 24B:
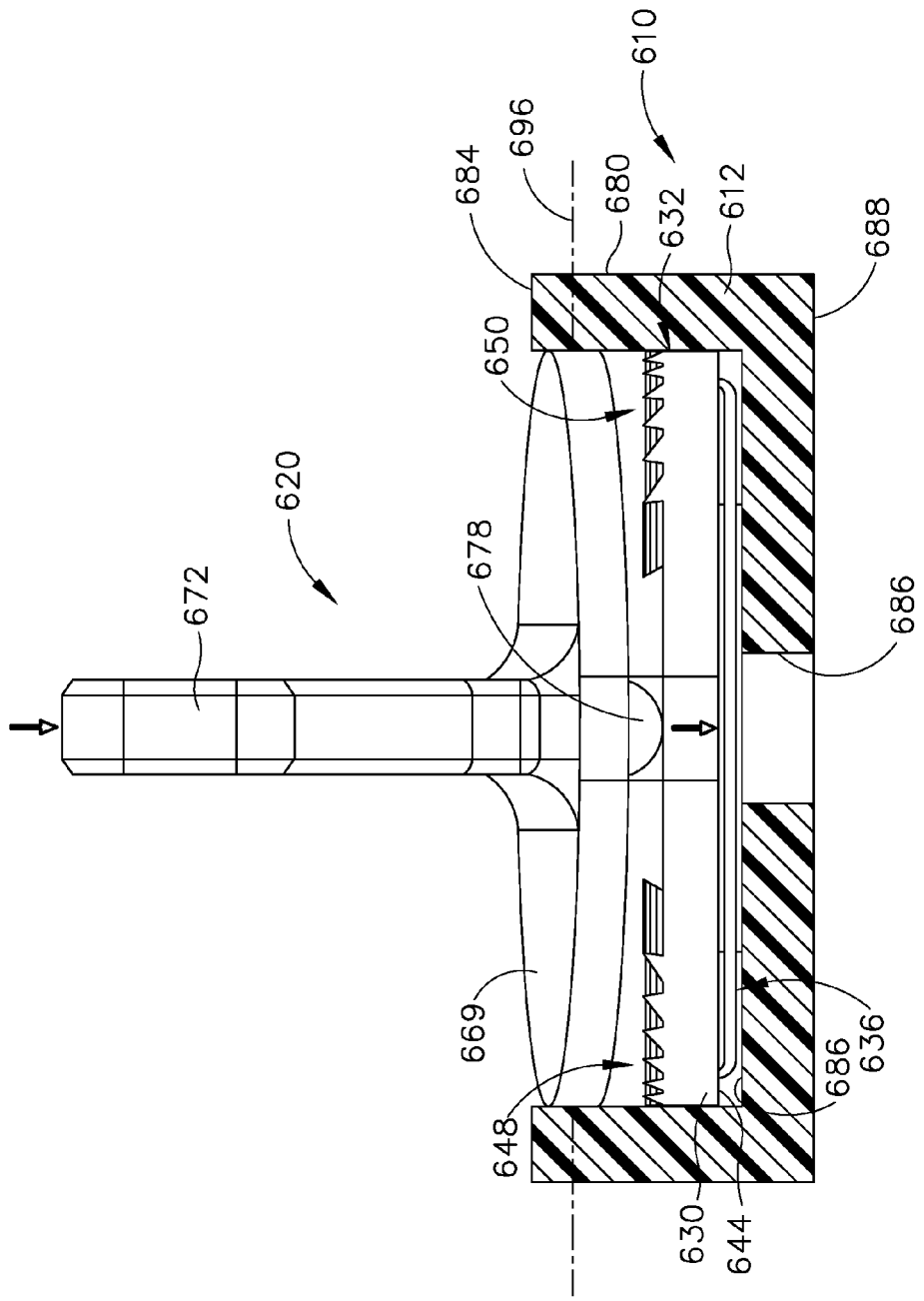
FIG. 24B shows a rear elevational view of the articulation control assembly of FIG. 20, with a portion of the housing hidden to show details of the components, and with the knob tilted to an unlocking position.

As best seen in FIG. 20, locking feature (630) of the present example includes a generally annular locking plate (632), a coil spring (634), and a wave spring (636). Annular locking plate (632) includes a radially outer edge (638), a radially inner edge (640), a first side (642) and a second side (644) (FIGS. 24A-B). Annular locking plate (632) further includes a pair of opposing male keying features (646a, 646b) extending radially outwardly from outer edge (638), a set of first locking teeth (648), and a set of second locking teeth (650). Each set of teeth (648, 650) has a sawtooth configuration and extends along only a respective portion of the angular range of first side (642).

Figure 21:
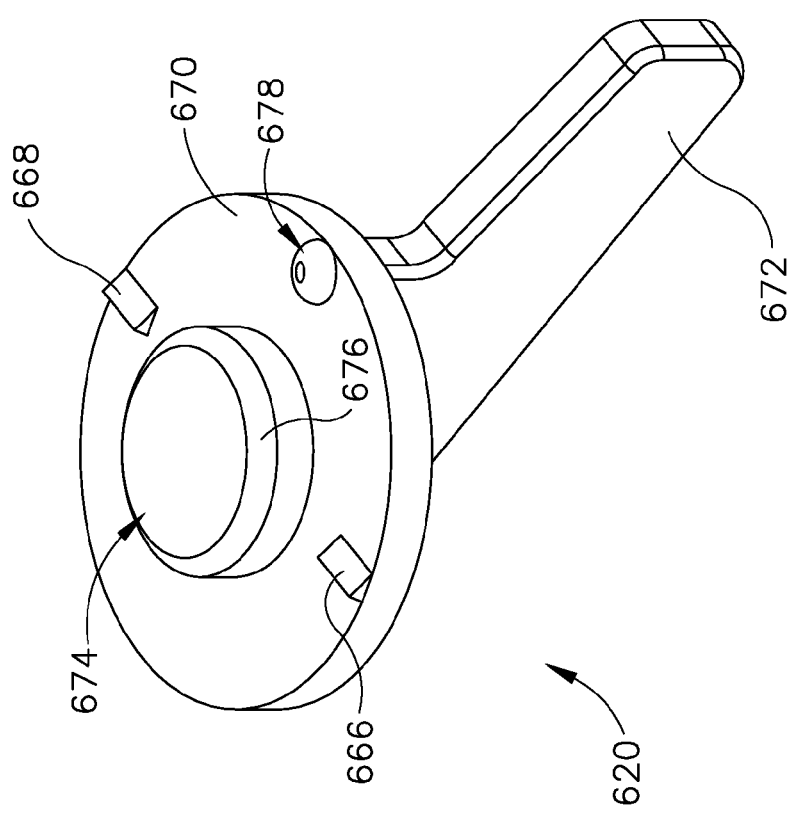
FIG. 21 depicts a bottom perspective view of a knob of the articulation control assembly of FIG. 20.

Different components of the locking feature (630) are also included on the knob (620) and housing (610). In particular, and as best seen in FIG. 21, knob (620) includes a first surface (669) and a second surface (670). A handle (672) extends upwardly from first surface (669). Teeth (666, 668) extend downwardly from second surface (670). Tooth (666) is angularly separated from tooth (668) by 180°. Teeth (666, 668) each have a sawtooth configuration such that teeth (666, 668) are configured to engage locking teeth (648, 650), respectively, to selectively lock the rotational position of knob (620) relative to housing (610). The complementary sawtooth configuration of tooth (666) and teeth (650) is such that tooth (666) may slide along teeth (650) in a ratcheting fashion as knob (620) is rotated in a first angular direction, yet the configuration of teeth (666, 650) will prevent knob (620) from rotating in a second angular direction (opposite to the first angular direction) when teeth (666, 650) are engaged. Likewise, the complementary sawtooth configuration of tooth (668) and teeth (648) is such that tooth (668) may slide along teeth (648) in a ratcheting fashion as knob (620) is rotated in the second angular direction, yet the configuration of teeth (668, 648) will prevent knob (620) from rotating in the first angular direction when teeth (668, 648) are engaged.

As also best seen in FIG. 21, knob (620) also includes a generally cylindrical projection (674) extending downwardly from surface (670) and having a chamfered edge (676). Cylindrical projection (674) is configured to engage a coil spring (634) as described below. Knob (620) further includes a generally hemispherical protrusion (678) extending downwardly from surface (670). Protrusion (678) is angularly positioned at 90° between teeth (666, 668). Protrusion (678) and handle (672) both lie along an imaginary vertical plane (679) (FIG. 24A) that laterally bisects knob (670). Plane (678) also laterally bisects handle (672) and protrusion (678).

In the present example, only a first cylindrical portion (612) of housing (610) is shown. It should be understood, however, that housing (610) may further include a second cylindrical portion (not shown) that is configured and operable substantially similar to second cylindrical portion (114) of articulation assembly housing (110). First cylindrical portion (612) of housing (610) is defined as a generally cylindraceous body having a generally cylindraceous cavity. Particularly, and as best seen in FIG. 20, cylindrical portion (612) includes a radially outer wall (680), a radially inner wall (682), an upper edge (684), and a generally circular inner surface (686). Radially inner wall (682) and inner surface (686) define a generally cylindraceous cavity (688) that also includes female keying features (690a, 690b) extending radially outward therefrom. An aperture (692) extends through surface (684) and through outer bottom surface (688). Aperture (692) provides a path for knob (620) to couple with features like translatable members (161, 162) to thereby drive articulation bands (140, 142) in opposing longitudinal directions in order to thereby drive articulation of articulation section (130).

As shown best in FIGS. 20 and 22-24B, locking plate (632), coil spring (634), and wave spring (636) are received in cavity (688). Particularly, locking plate (632), coil spring (634), and wave spring (636) are situated in cavity (688) in a coaxial arrangement. Wave spring (636) abuts surface (686). Locking plate (632) is positioned above wave spring (636) such that portions of surface (644) of locking plate (632) abut wave spring (636). Female keying portions (690a, 690b) of first cylindrical portion (612) receive male keying portions (646a, 646b) of locking plate (632). The relationship between keying portions (646a, 646b, 690a, 690b) permits locking plate (632) to translate vertically within first cylindrical portion (612) but prevents locking plate (632) from rotating relative to first cylindrical portion (612). Coil spring (634) is sized such that the effective outer diameter of coil spring (634) is less than the inner diameter defined by radially inner edge (640) of locking plate (632).

Knob (620) is placed relative to the cavity (688) such that locking plate (632) is generally interposed between knob (620) and wave spring (636). Moreover, knob (620) is placed relative to the cavity such that surface (669) of knob (620) is generally flush with edge (684) of cylindrical portion (612). A retention feature (not shown) is provided in order prevent knob (620) from moving above edge (684) to a point where surface (669) is above edge (684). For instance, after the above components are assembled together, a retaining ring may be placed over edge (684) to restrict upward vertical movement of knob (620) relative to first cylindrical portion (612). Coil spring (634) is further sized such that the effective inner diameter of coil spring (634) is less than the outer diameter of cylindrical projection (674) of knob (620). Coil spring (634) thus receives cylindrical projection (674) such that cylindrical projection (674) maintains the axial orientation of coil spring (634) within first cylindrical member (612).

Figure 22:
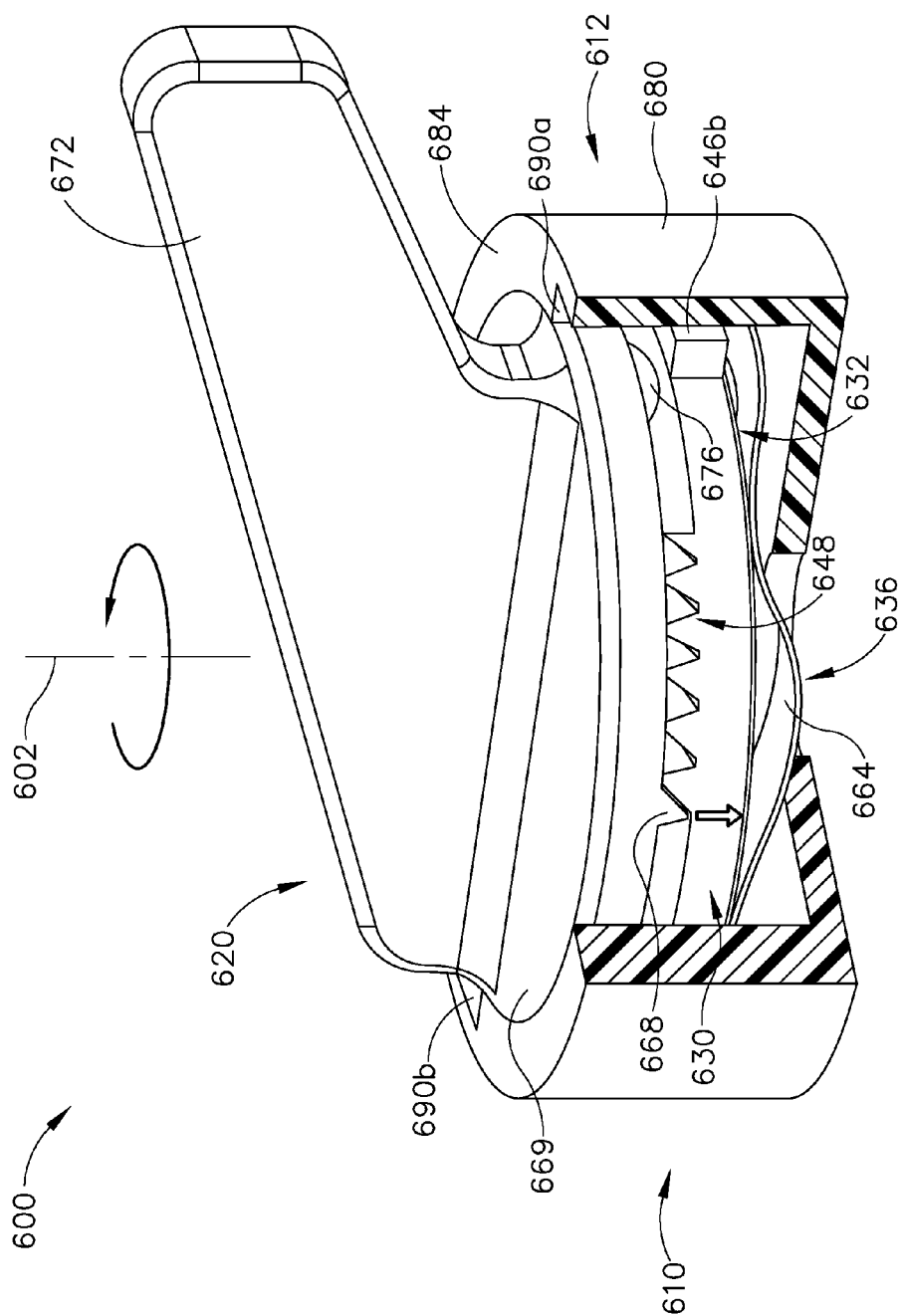
FIG. 22 depicts a perspective view of the articulation control assembly of FIG. 20, with part of the housing broken away to show details of the components.
Figure 23:
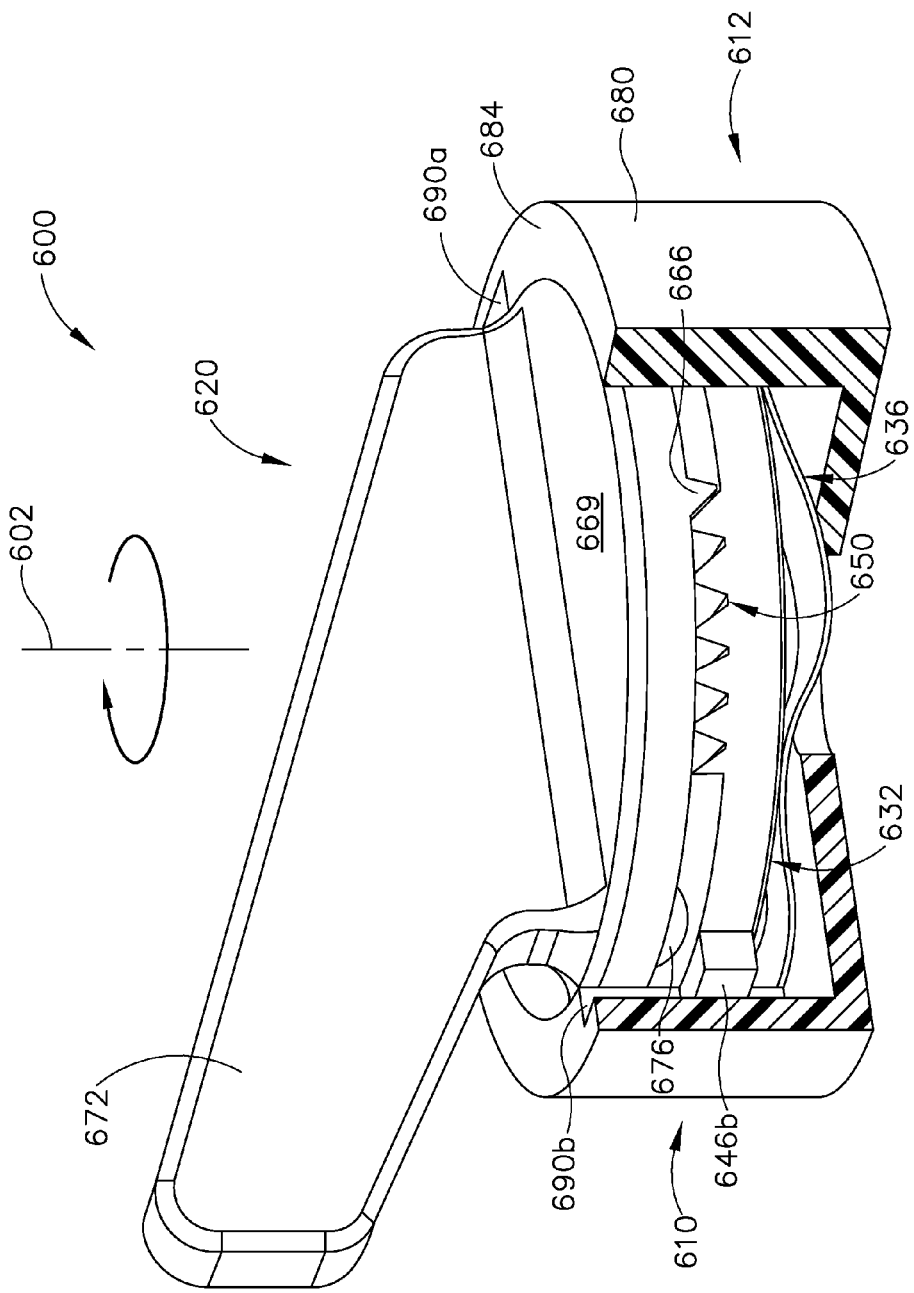
FIG. 23 depicts another perspective view of the articulation control assembly of FIG. 20, with part of the housing broken away to show details of the components.

As shown in FIGS. 22-23, knob (620) is initially placed such that locking teeth (666, 668) are adjacent to but do not yet engage the detent features (648, 650), respectively. Knob (620) is horizontally oriented such that surfaces (669, 670) are parallel to sides (642, 644) of locking plate (632) and inner surface (686) of cylindrical portion (612). At this point, knob (620) is free to rotate relative to housing (610) in either a first direction or second direction about a vertical axis (602) in order to articulate the articulation section in a first or second direction. For example, rotation of knob (620) from the neutral position shown in FIGS. 22-23 in a first angular direction about axis (602) will cause articulation of the articulation section in a first direction. As knob (620) is rotated in the first direction, tooth (668) ratchets along teeth (648). Tooth (666) simply slides along (or moves freely above) first side (642) of locking plate (632). When the operator thereafter releases knob (620), engagement between teeth (668, 648) will lock the articulation section in the selected state of articulation. In other words, engagement between teeth (668, 648) will lock articulation control assembly (600), thereby locking the articulation section in an articulated state.

Similarly, rotation of knob (620) from the neutral position shown in FIGS. 22-23 in a second angular direction about axis (602) will cause articulation of the articulation section in a second direction. As knob (620) is rotated in the second direction, tooth (666) ratchets along teeth (650). Tooth (668) simply slides along (or moves freely above) first side (642) of locking plate (632). When the operator thereafter releases knob (620), engagement between teeth (666, 650) will lock the articulation section in the selected state of articulation. In other words, engagement between teeth (666, 650) will lock articulation control assembly (600), thereby locking the articulation section in an articulated state.

Figure 25:
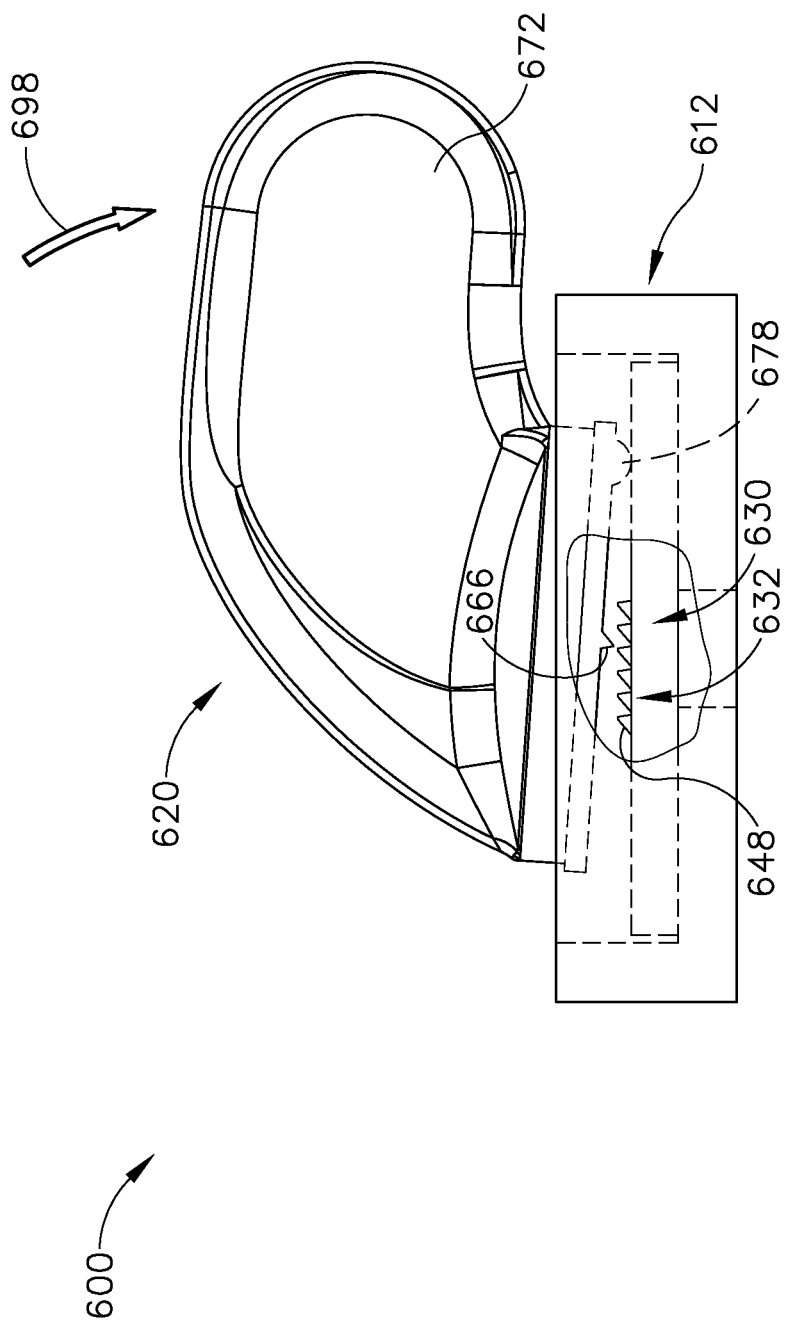
FIG. 25 shows a side elevational view of the articulation control assembly of FIG. 20, with a portion of the housing being shown as transparent to show details of the components, and with the knob tilted to the unlocking position.

When the operator wishes to unlock articulation control assembly (600) and the articulation section (e.g., to return the articulation section to a straight configuration), the operator may tilt the proximal end of knob (620) downwardly about a horizontal axis (696) as shown in FIGS. 24A-25. In particular, FIG. 24A shows articulation control assembly (600) before knob (620) is tilted, while articulation control assembly (600) is still in a locked state. As the proximal end of knob (620) is tilted downwardly about horizontal axis (696), protrusion (678) bears downwardly on first side (642) of locking plate (632), thereby driving locking plate (632) downwardly as shown in FIGS. 24B and 25. As locking plate (632) is driven downwardly, whichever tooth (666, 668) that was previously engaged with the corresponding teeth (650, 648) will disengage teeth (650, 648), thereby transitioning articulation control assembly (600) to an unlocked state. While holding knob (620) in the tilted orientation, the operator may rotate knob (620) in either direction about axis (602) to re-adjust the state of articulation of the articulation section. Once the articulation section has reached the desired re-adjusted state, the operator may release knob (620). At this point, the resilience of coil spring (634) will drive knob (620) back to the horizontal orientation shown in FIGS. 22-24A.

Figure 26A:
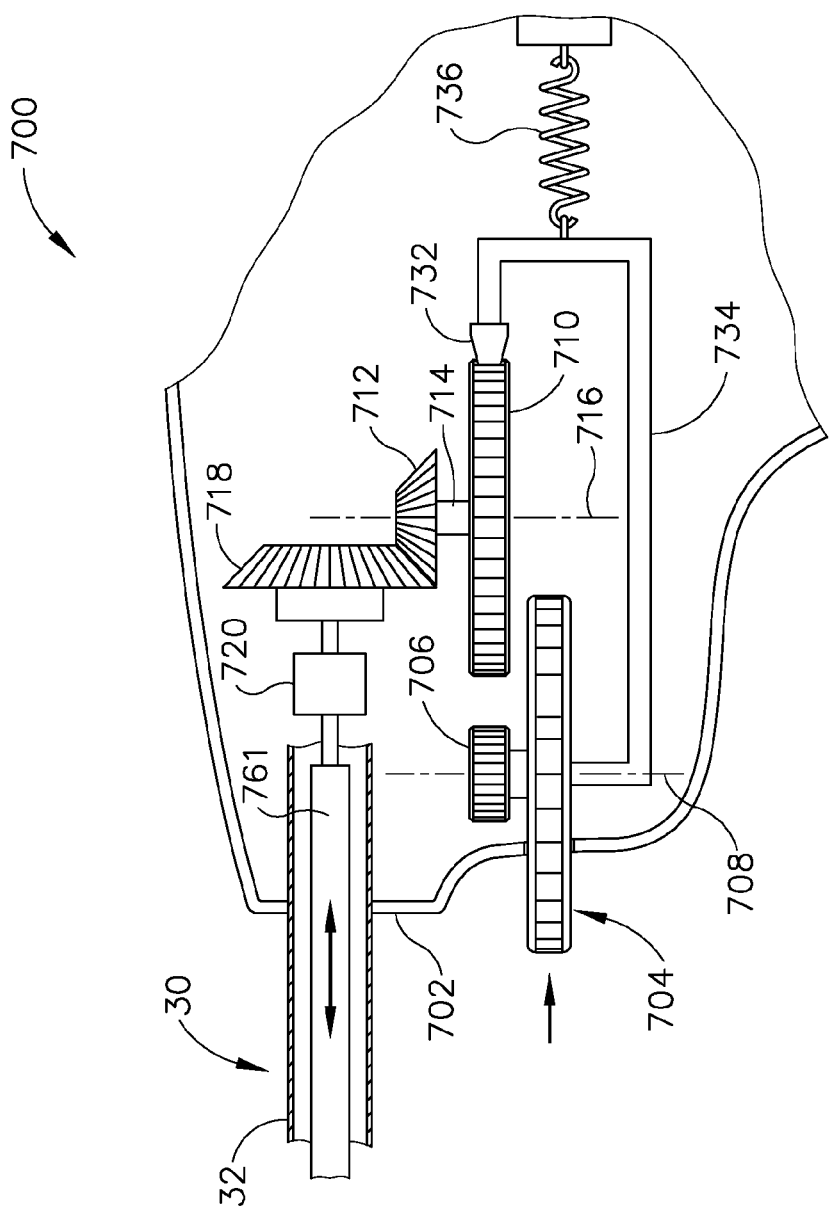
FIG. 26A depicts a partial, schematic, side elevational view of an exemplary alternative articulation control assembly that may be incorporated into the instrument of FIG. 1, with a locking feature in a locked configuration.
Figure 26B:
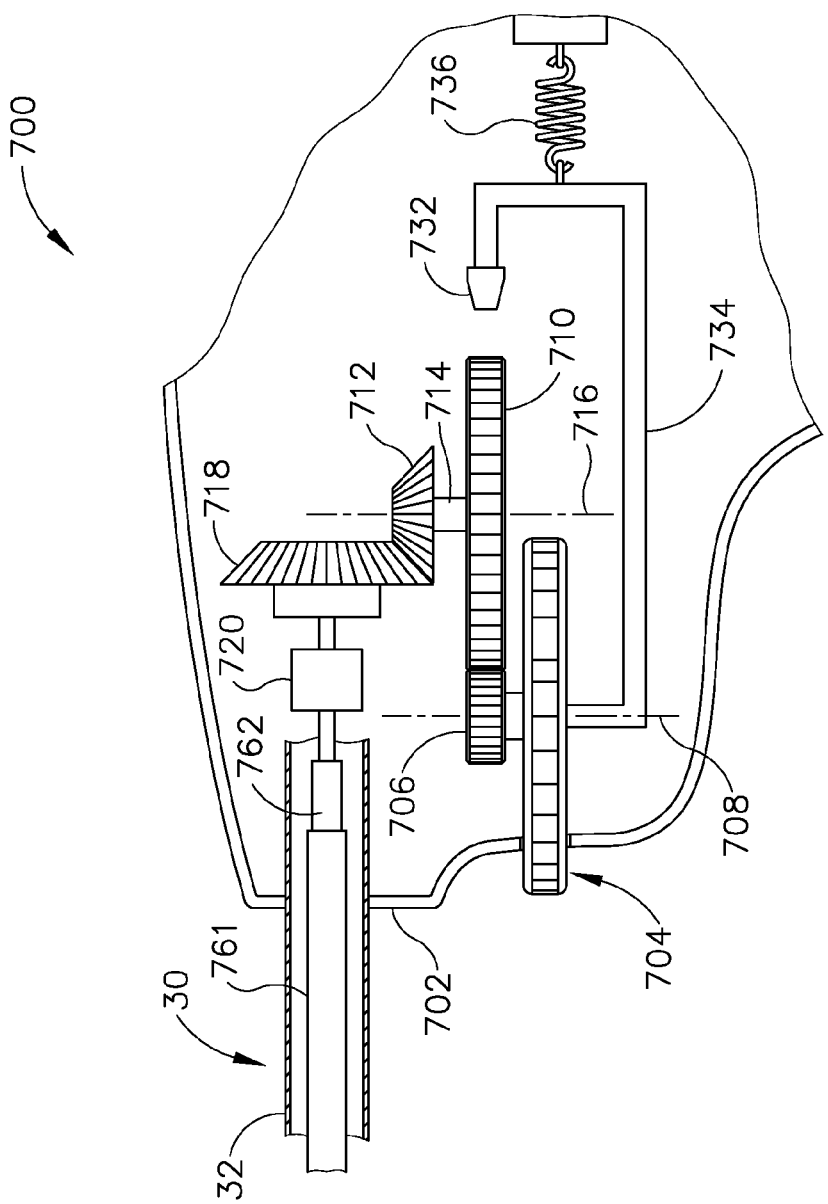
FIG. 26B depicts a partial, schematic, side elevational view of the articulation control assembly of FIG. 26A, with the locking feature in an unlocked configuration.
Figure 27A:
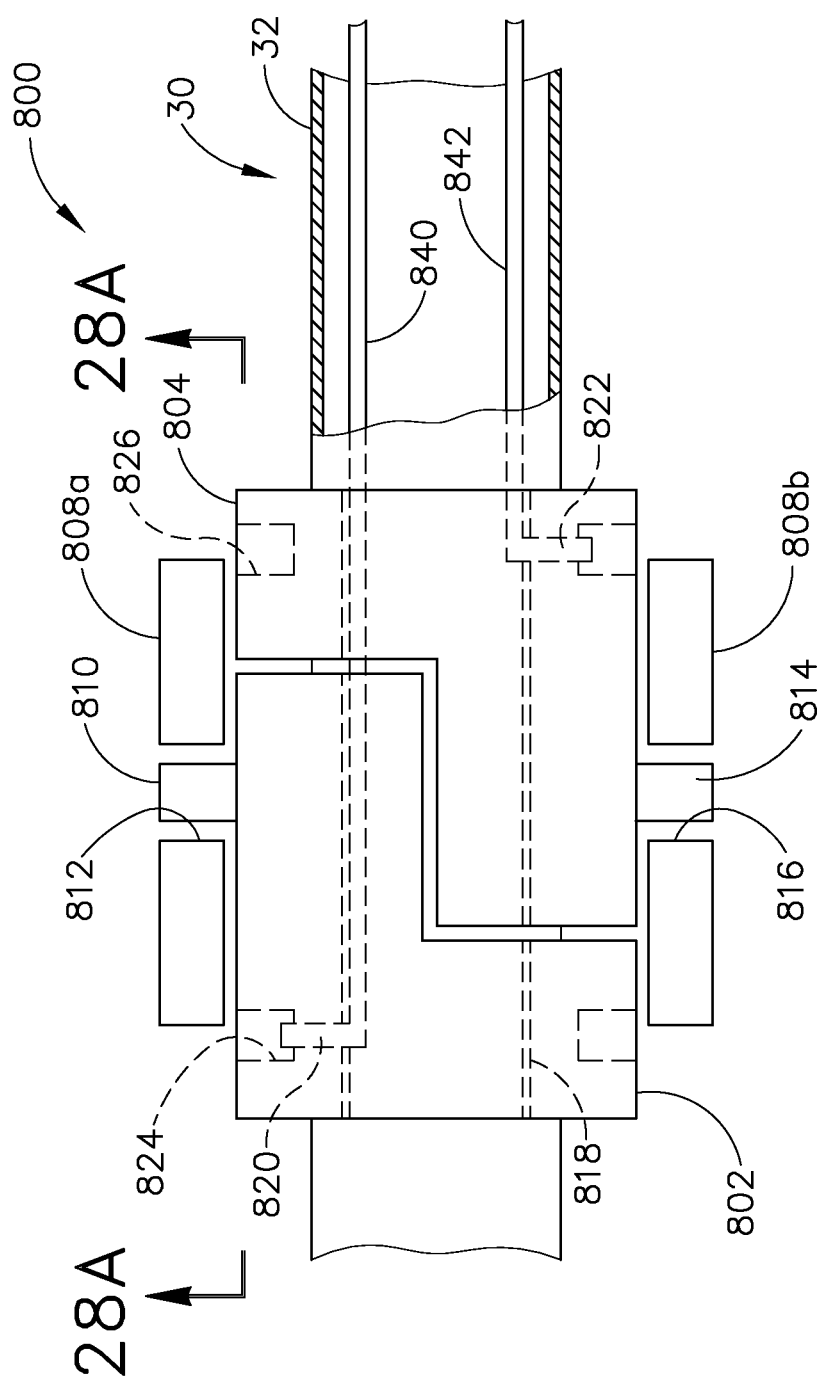
FIG. 27A depicts a top plan view of another exemplary alternative articulation control assembly that may be incorporated into the instrument of FIG. 1, with the articulation control assembly in a first configuration.
Figure 27B:
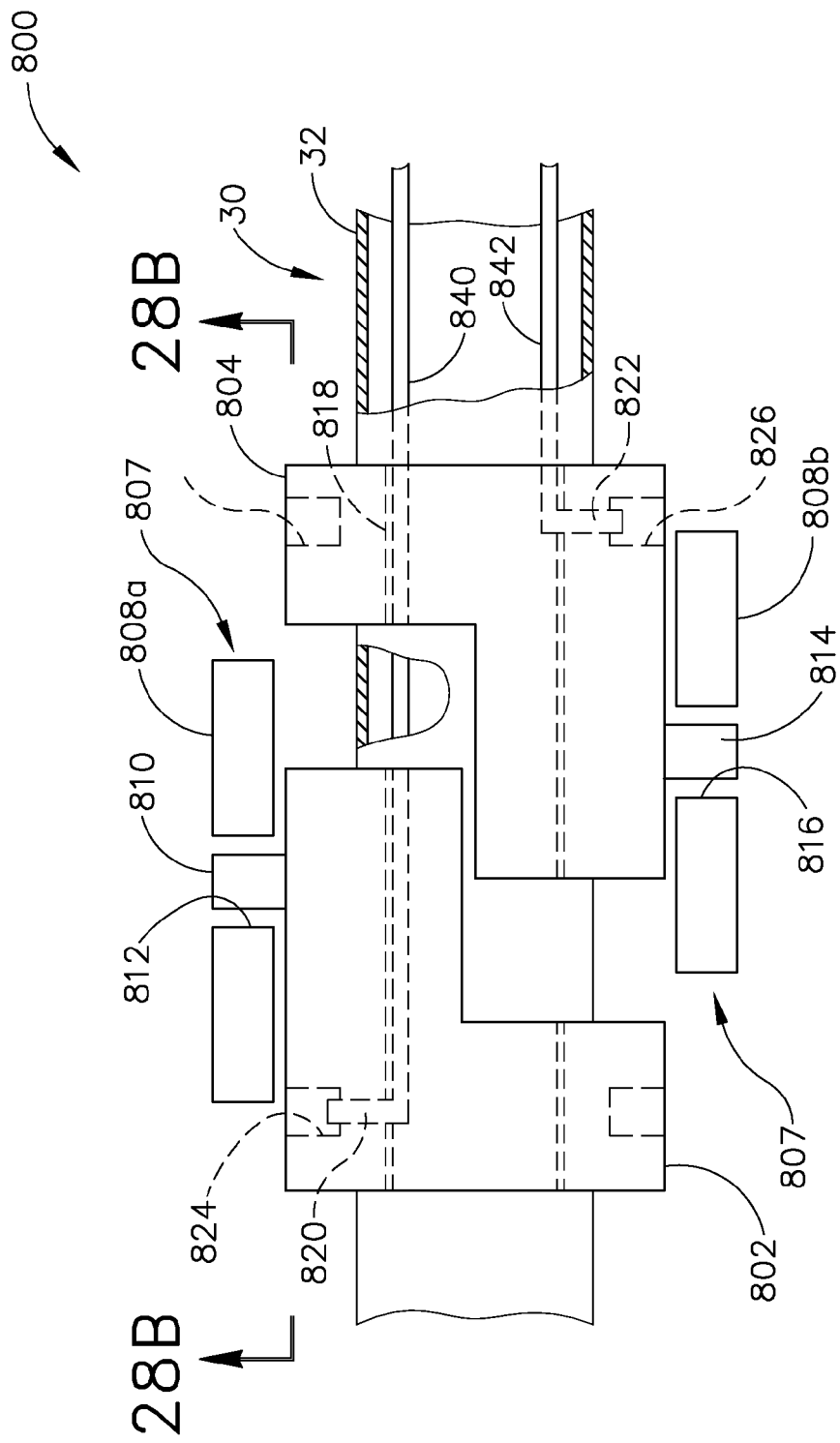
FIG. 27B depicts a top plan view of the articulation control assembly of FIG. 27A, with the articulation control assembly in a second configuration.

F. Articulation Control Assembly with Resiliently Biased Control Wheel and Locking Feature FIGS. 26A-26B show exemplary alternative articulation control assembly (700) that may be readily incorporated into instrument (10) in place of articulation control assembly (100). Articulation control assembly (700) of the present example is configured to articulate articulation section (130) in a substantially similar manner to articulation control assembly (100), except for the differences described below. Articulation control assembly (700) is secured to a proximal portion of outer sheath (32) of shaft assembly (30). Articulation control assembly (700) is located within a body (702) of a handle assembly. Except as otherwise described herein, body (702) and the rest of the handle assembly may be configured similar to body (22) and the rest of handle assembly (20) of instrument (10).

Articulation control assembly (700) of the present example includes a rotatable input wheel (704) that is configured to translate and rotate relative to body (702). Input wheel (704) includes an integral gear (706). Wheel (704) and gear (706) are rotatable about an axis (708). Wheel (704) and gear (706) are further coupled with a rigid arm (734). Arm (734) is further coupled with a pawl (732) and a resilient member (736). Resilient member (736) is mounted to body (702) and is configured to bias wheel (704) and gear (706) to the position shown in FIG. 26A.

Articulation control assembly (700) of the present example further includes a transmission gear (710), a first bevel gear (712), and a second bevel gear (718). Transmission gear (710) and first bevel gear (712) are unitarily coupled together via a shaft (714), such that gears (710, 712) rotate together unitarily. Bevel gears (712, 718) are in a meshing relationship with each other, such that rotation of first bevel gear (712) will provide rotation of second bevel gear (718). Second bevel gear (718) is coupled with an opposing thread transmission assembly (720), which is further coupled with translating members (761, 762). Transmission assembly (720) is configured to convert a rotary output from second bevel gear (718) into opposing longitudinal motion of translating members (761, 762). Translating members (761, 762) are coupled with respective articulation bands similar to articulation bands (140, 142), such that opposing longitudinal motion of translating members (761, 762) provides articulation of an articulation section in a shaft assembly.

In some versions, transmission assembly (720) comprises a first nut and lead screw assembly associated with first translating member (761); and a second nut and lead screw assembly associated with second translating member (761). The second nut and lead screw assembly may have a thread orientation that is opposite from the thread orientation of the first nut and lead screw assembly, such that the lead screw assemblies may provide opposing longitudinal motion from a single rotary input that is shared by both of the lead screw assemblies. By way of example only, transmission assembly (720) may be configured in accordance with at least some of the teachings of U.S. Pub. No. 2013/0023868, entitled "Surgical Instrument with Contained Dual Helix Actuator Assembly," published Jan. 24, 2013, now U.S. Pat. No. 9,545,253, issued Jan. 17, 2017, the disclosure of which is incorporated by reference herein. Other suitable configurations for transmission assembly (720) will be apparent to those of ordinary skill in the art in view of the teachings herein.

Articulation control assembly (700) is configured to transition between a locked state (FIG. 26A) and a driving state (FIG. 26B). In the locked state, gear (706) is disengaged from gear (710) and pawl (732) is engaged with gear (710). Pawl (732) prevents gear (710) from rotating. With gear (710) locked by pawl (732), gears (712, 718) and transmission assembly (720) are also locked. With transmission assembly (720) locked, translating members (761, 762) are also locked, thereby locking the articulation section in its current state of articulation. If the operator attempts to rotate wheel (704) about axis (708) when articulation control assembly (700) is in the locked state, wheel (704) will simply rotate freely without having any other effect. Alternatively, body (702) may include an integral pawl feature that engages wheel (704) or gear (706) when articulation control assembly (700) is in the locked state. Such a pawl may prevent wheel (704) from rotating when articulation control assembly (700) is in the locked state, thereby providing tactile feedback to the operator to indicate that articulation control assembly (700) is in the locked state.

When the operator wishes to change the articulation state of the articulation section (e.g., articulation section (130), described above), the operator may transition articulation control assembly (700) to the driving state by pushing/pulling wheel (704) proximally from the position shown in FIG. 26A to the position shown in FIG. 26B. This will eventually bring gear (706) into engagement with gear (710). In addition, the proximal movement of wheel (704) will be communicated to pawl (732) via arm (734), such that pawl (732) will disengage gear (710) as shown in FIG. 26B. The proximal movement of arm (734) also compresses resilient member (736). With pawl (732) disengaged from gear (710), gear (710) is free to rotate. With gear (706) engaged with gear (710), rotation of wheel (704) will cause rotation of gear (710). It should therefore be understood that rotation of wheel (704) will actuate transmission assembly (720), thereby providing opposing longitudinal motion of translating members (761, 762), when articulation control assembly (700) is in the driving as shown in FIG. 26B. In other words, rotation of wheel (704) about axis (708) will drive articulation of the articulation section of the shaft assembly when articulation control assembly (700) is in the driving as shown in FIG. 26B.

Once the operator has achieved the desired state of articulation in the articulation section of the shaft assembly, the operator may simply release wheel (704). When the operator releases wheel (704), resilient member (736) will drive wheel (704), gear (706), and pawl (732) back to the positions shown in FIG. 26A, thereby transitioning articulation control assembly (700) back to the locked state. This will lock the articulation assembly in the adjusted state of articulation. Various other suitable ways in which articulation control assembly (700) may be configured and operated will be apparent to a person skilled in the art in view of the teachings herein.

G. Articulation Control Assembly with Self-Locking Linear Cam Features

FIGS. 27A-28B show another exemplary alternative articulation control assembly (800) that may be readily incorporated into instrument (10) in place of articulation control assembly (100). Articulation control assembly (800) is configured to articulate articulation section (130) in a substantially similar manner to articulation control assembly (100), except for the differences described below. Articulation control assembly (800) is secured to a proximal portion of outer sheath (32) of shaft assembly (30).

Figure 28A:
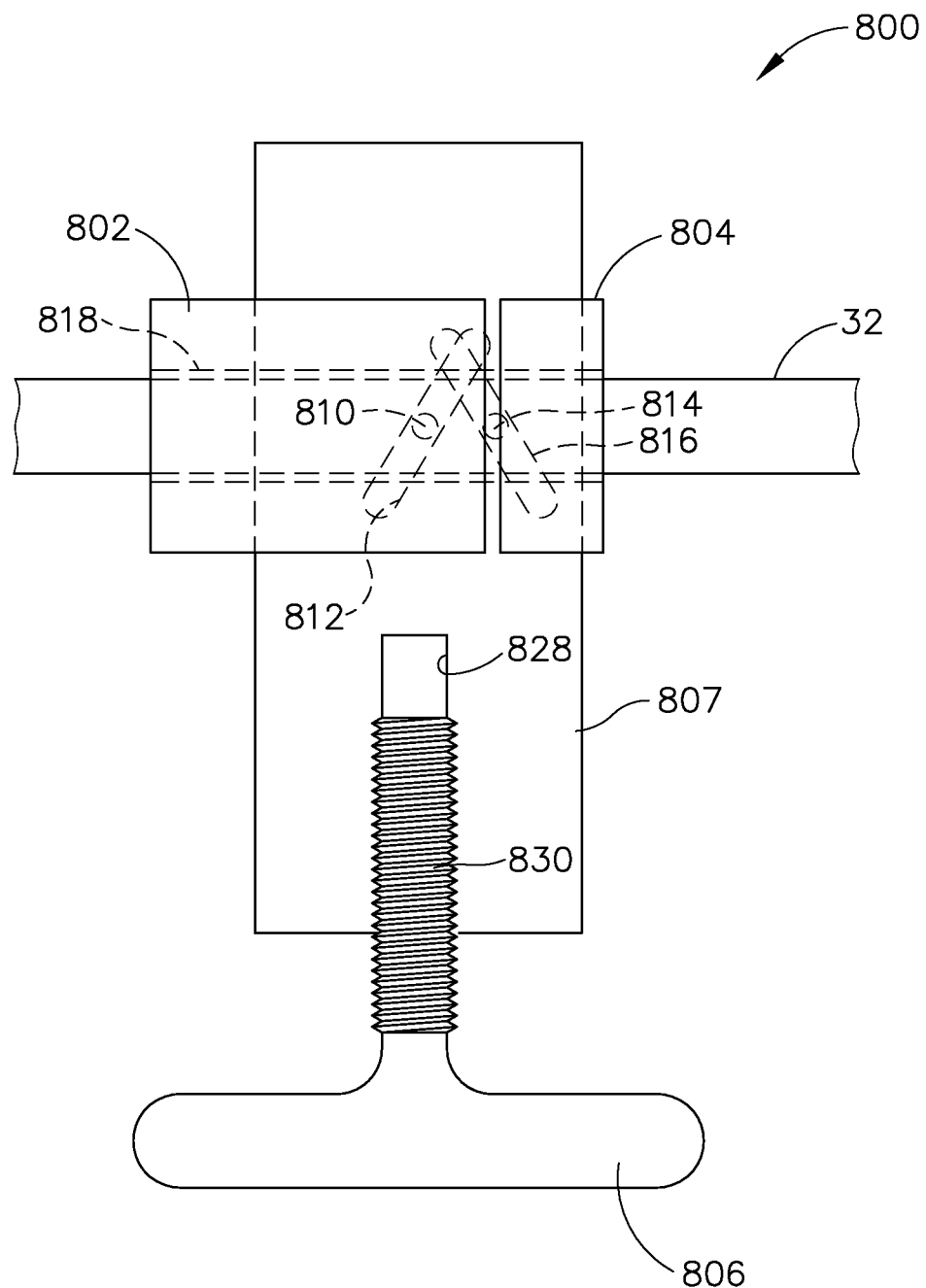
FIG. 28A depicts a partial side elevational view of the articulation control assembly of FIG. 27A, with the articulation control assembly in the first configuration.
Figure 28B:
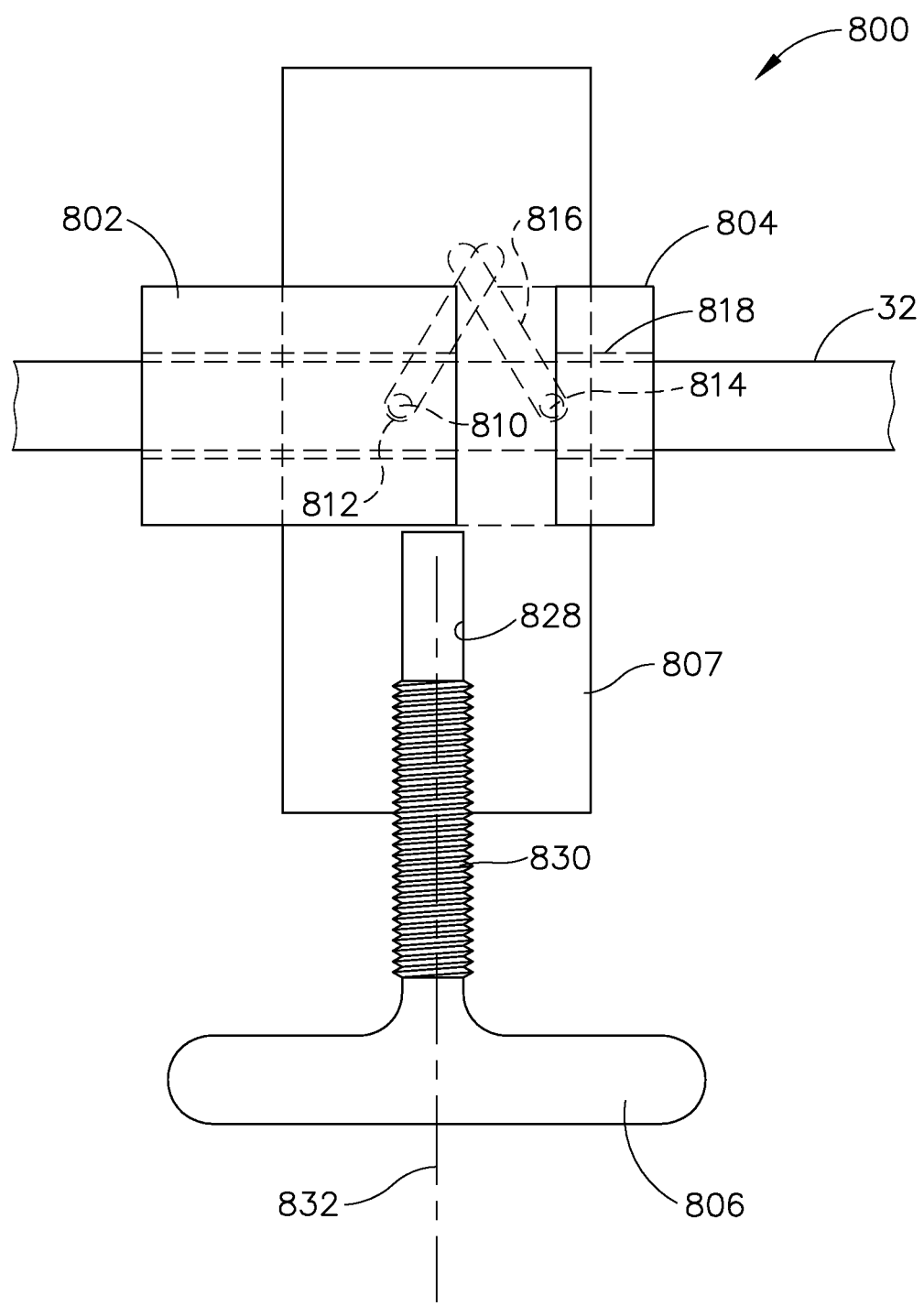
FIG. 28B depicts a partial side elevational view of the articulation control assembly of FIG. 27B, with the articulation control assembly in the second configuration.
Figure 29A:
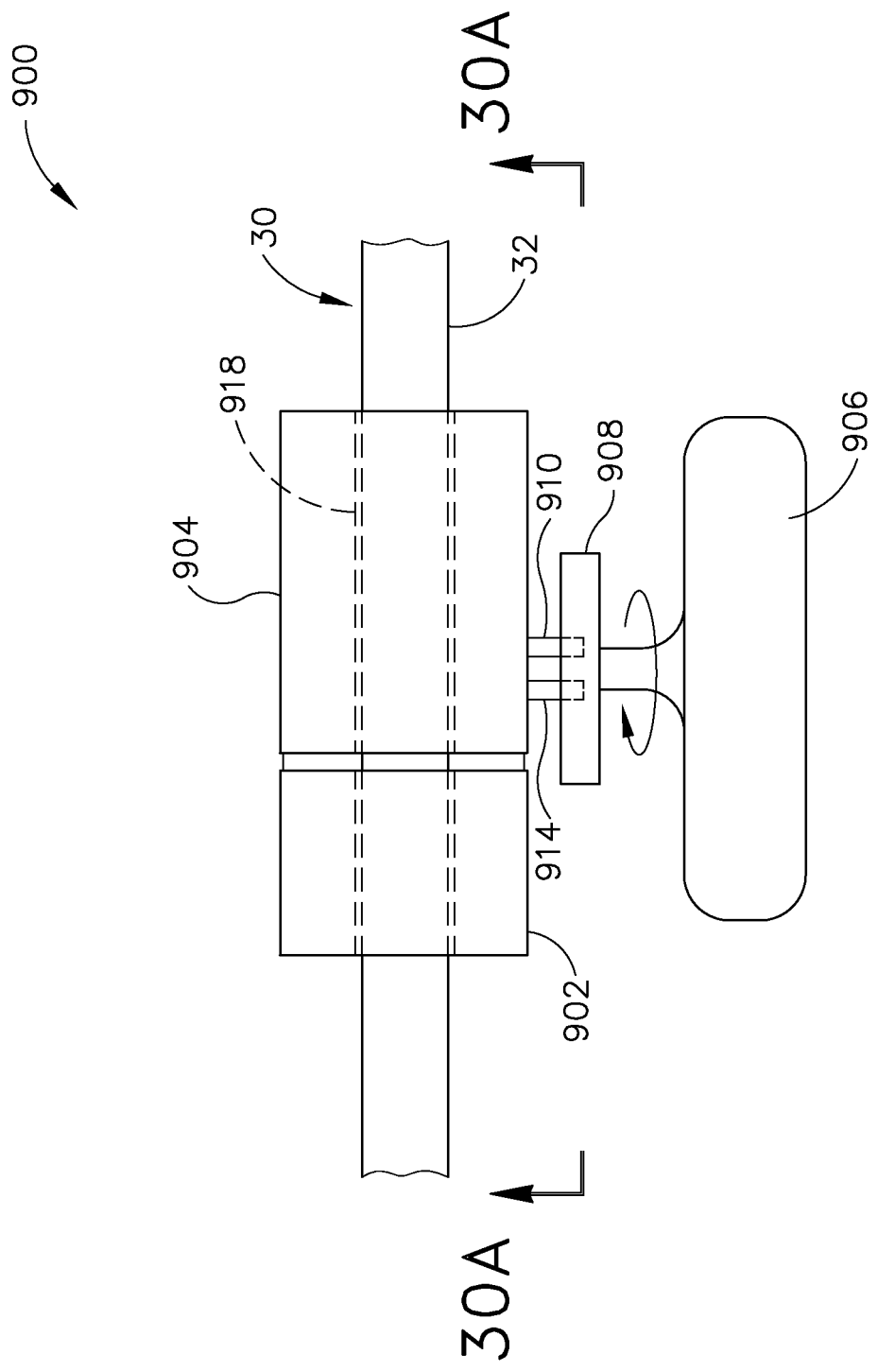
FIG. 29A depicts a side elevational view of another exemplary alternative articulation control assembly that may be incorporated into the instrument of FIG. 1, with the articulation control assembly in a first configuration.
Figure 29B:
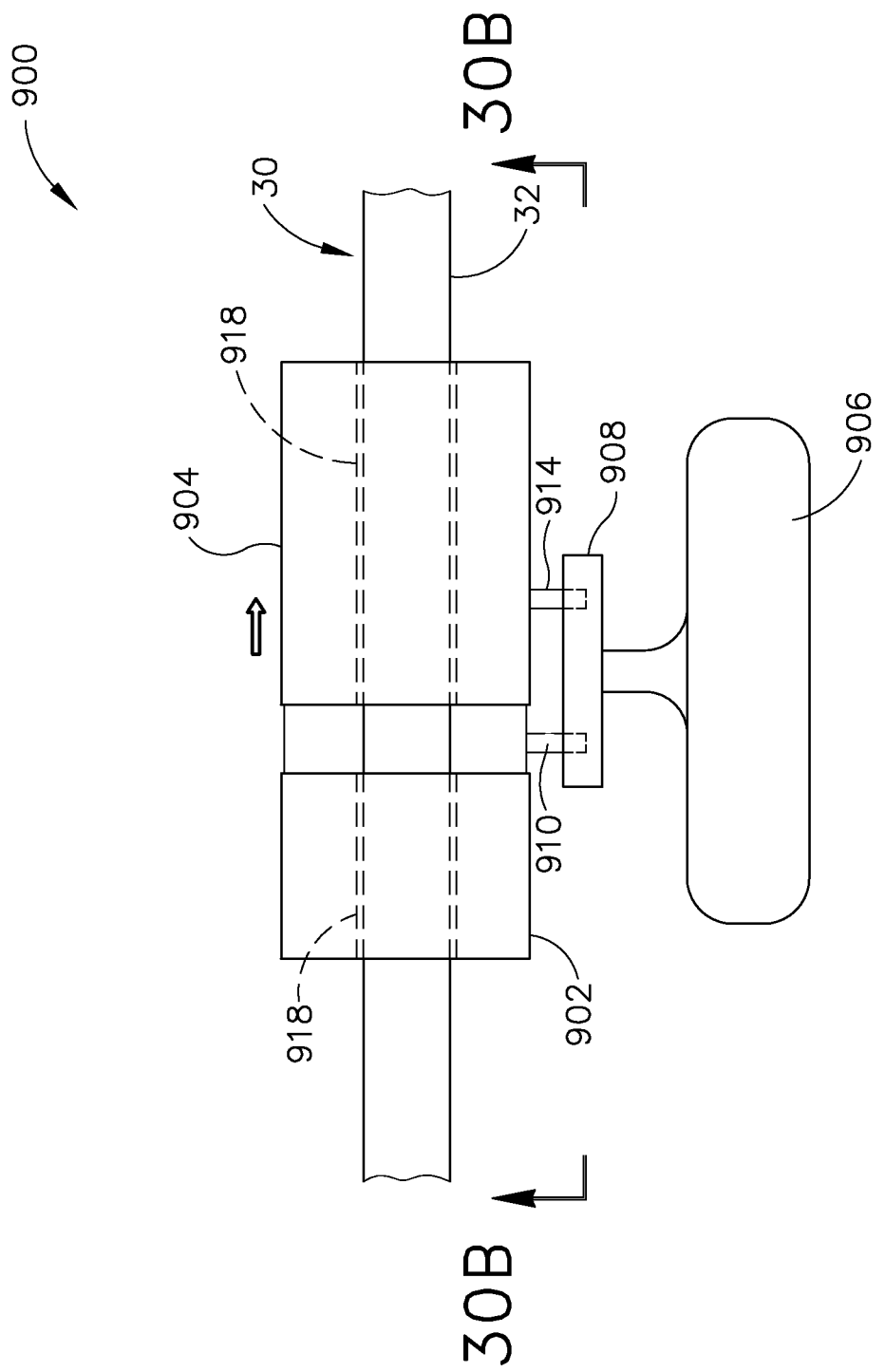
FIG. 29B depicts a side view of the articulation control assembly of FIG. 29A, with the articulation control assembly in a second configuration.

In the present example, articulation control assembly (800) comprises a first collar (802), a second collar (804), and a rotatable knob (806). Rotation of knob (806) causes the articulation of articulation section (130), as discussed in more detail below. Articulation control assembly (900) further includes an actuator (807) with opposing first and second cam plates (808a, 808b). First collar (802) includes a first pin (810) extending transversely therefrom. First pin (810) is received in a first cam channel (812) of cam plate (808a). Second collar (804) includes a second pin (814) extending transversely therefrom. Second pin (814) is received in a second cam channel (816) of cam plate (808). As best seen in FIGS. 28A-28B, cam channels (812, 816) each extend obliquely relative to a vertical axis (832). In addition, first cam channel (812) tilts distally while second cam channel (816) tilts proximally.

Shaft assembly (30) comprises a pair of articulation bands (840, 842) that are coupled to first and second collars (802, 804) via pins (820, 822), respectively. Articulation bands (840, 842) are configured to operate substantially similar to articulation bands (140, 142), such that opposing longitudinal translation of articulation bands (840, 842) causes articulation of articulation section (130). Articulation bands (840, 842) extend slidably and longitudinally through the proximal portion of outer sheath (32). Pin (820) is received within annular groove (824) of first collar (802), and pin (822) is received within annular groove (826) of second collar (804). Thus, as shaft assembly (30) rotates relative to articulation control assembly (800), pin (820) rotates within annular groove (824), and pin (822) rotates within annular groove (826). Pins (820, 822) are mechanically coupled with respective articulation bands (840, 842), respectively, such that longitudinal translation of pin (820) causes longitudinal translation of articulation band (840), and such that longitudinal translation of pin (822) causes longitudinal translation of articulation band (842).

Actuator (807) of the present example includes a threaded bore (828) that is configured to threadably couple with a threaded rod (830) that is coupled to knob (806). Knob (806) and threaded rod (830) are fixed together along an axis (832) such that rotation of knob (806) causes actuator to move longitudinally along axis (832) due to the threaded coupling between threaded rod (830) and actuator (807). For example, rotating knob (806) in a first direction causes actuator (807) to move in a direction away from knob (806) along axis (832), and along a plane that is perpendicular to the longitudinal axis of outer sheath (32). Rotating knob (806) in a second direction causes actuator (807) to move toward knob (807) along axis (832), and along a plane that is perpendicular to the longitudinal axis of outer sheath (32).

As shown in the transition from FIG. 28A to FIG. 28B, knob (806) has been rotated in a direction that has caused actuator (807) to move away from knob (806). Due to the configuration of cam channels (812, 816), the movement of actuator (807) away from knob (806) causes pins (810, 814) to follow cam channels (812, 816). Thus, pin (810) is urged in a proximal direction by cam channel (812), thereby causing proximal translation of collar (802). Similarly, pin (814) is urged in a distal direction by cam channel (816), thereby causing distal translation of collar (804). Due to the coupling engagement between collar (902) and articulation band (940), the proximal translation of collar (802) causes the proximal translation of articulation band (840). Similarly, due to the coupling engagement between collar (804) and articulation band (842), the distal translation of collar (804) causes the distal translation of articulation band (842). Thus, articulation bands (840, 842) translate simultaneously in opposing longitudinal directions in response to rotation of knob (806). Rotation of knob (806) will thereby change the articulation state of articulation section (130).

It should be understood that pins (810, 814) and cam channels (812, 816) may be positioned and arranged such that rotation of knob (806) in a first angular direction will cause articulation section (130) to deflect in a first lateral direction away from the longitudinal axis of outer sheath (32); while rotation of knob (806) in a second angular direction will cause articulation section (130) to deflect in a second lateral direction away from the longitudinal axis of outer sheath (32). It should also be understood that, due to the configuration and arrangement of pins (810, 814) and cam channels (812, 816), articulation control assembly (800) may provide self-locking of articulation section (130). In other words, friction between pins (810, 814) and cam channels (812, 816) may prevent articulation section (130) from inadvertently deflecting away from a selected state of articulation unless and until the operator rotates knob (806).

H. Articulation Control Assembly with Self-Locking Rotary Cam Features

FIGS. 29A-30B show another exemplary alternative articulation control assembly (900) that may be readily incorporated into instrument (10) in place of articulation control assembly (100). Articulation control assembly (900) is configured to articulate articulation section (130) in a substantially similar manner to articulation control assembly (100), except for the differences described below. Articulation control assembly (900) is secured to a proximal portion of outer sheath (32) of shaft assembly (30).

Articulation control assembly (900) comprises a first collar (902), a second collar (904), a rotatable knob (906), and a cam plate (908). Cam plate (908) is coupled to rotatable knob (906) such that rotation of rotatable knob (906) causes rotation of cam plate (908). First collar (902) includes a first pin (910) extending transversely therefrom. First pin (910) is received in a first cam channel (912) of cam plate (908). Second collar (904) includes a second pin (914) extending transversely therefrom. Second pin (914) is received in a second cam channel (916) of cam plate (908).

Shaft assembly (30) comprises a pair of articulation bands (940, 942) that are coupled to first and second collars (902, 904) via pins (920, 922), respectfully. Articulation bands (940, 942) are configured to operate substantially similar to articulation bands (140, 142), such that opposing longitudinal translation of articulation bands (940, 942) causes articulation of articulation section (130). Articulation bands (940, 942) extend slidably and longitudinally through the proximal portion of outer sheath (32). Pin (920) is received within annular groove (924) of first collar (902), and pin (922) is received within annular groove (926) of second collar (904). Thus, as shaft assembly (30) rotates relative to articulation control assembly (900), pin (920) rotates within annular groove (924) and pin (922) rotates within annular groove (926). Pins (920, 922) are mechanically coupled with respective articulation bands (940, 942) such that longitudinal translation of pin (920) causes longitudinal translation of articulation band (940), and such that longitudinal translation of pin (922) causes longitudinal translation of articulation band (942).

Figure 30A:
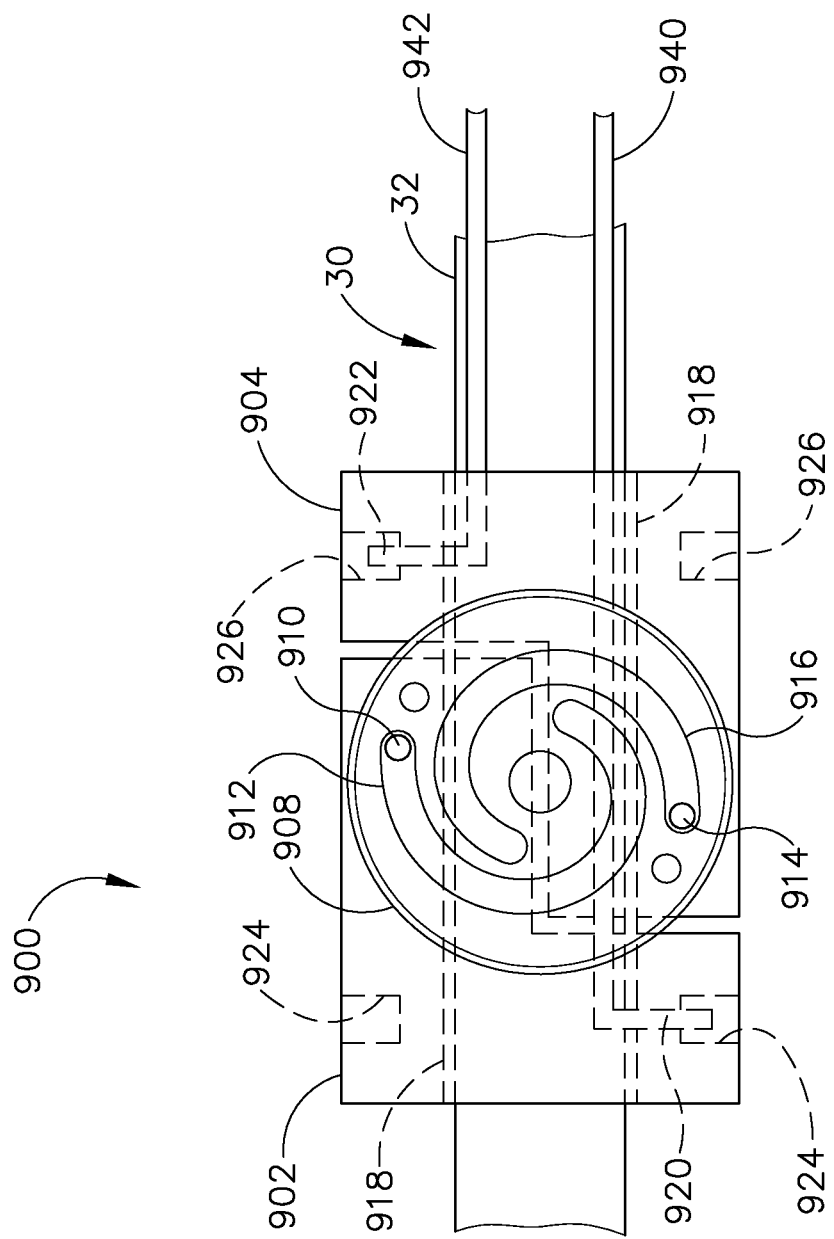
FIG. 30A depicts a partial cross-sectional view of the articulation control assembly of FIG. 29A, taken along line 30A-30A of FIG. 29A, with the articulation control assembly in the first configuration.
Figure 30B:
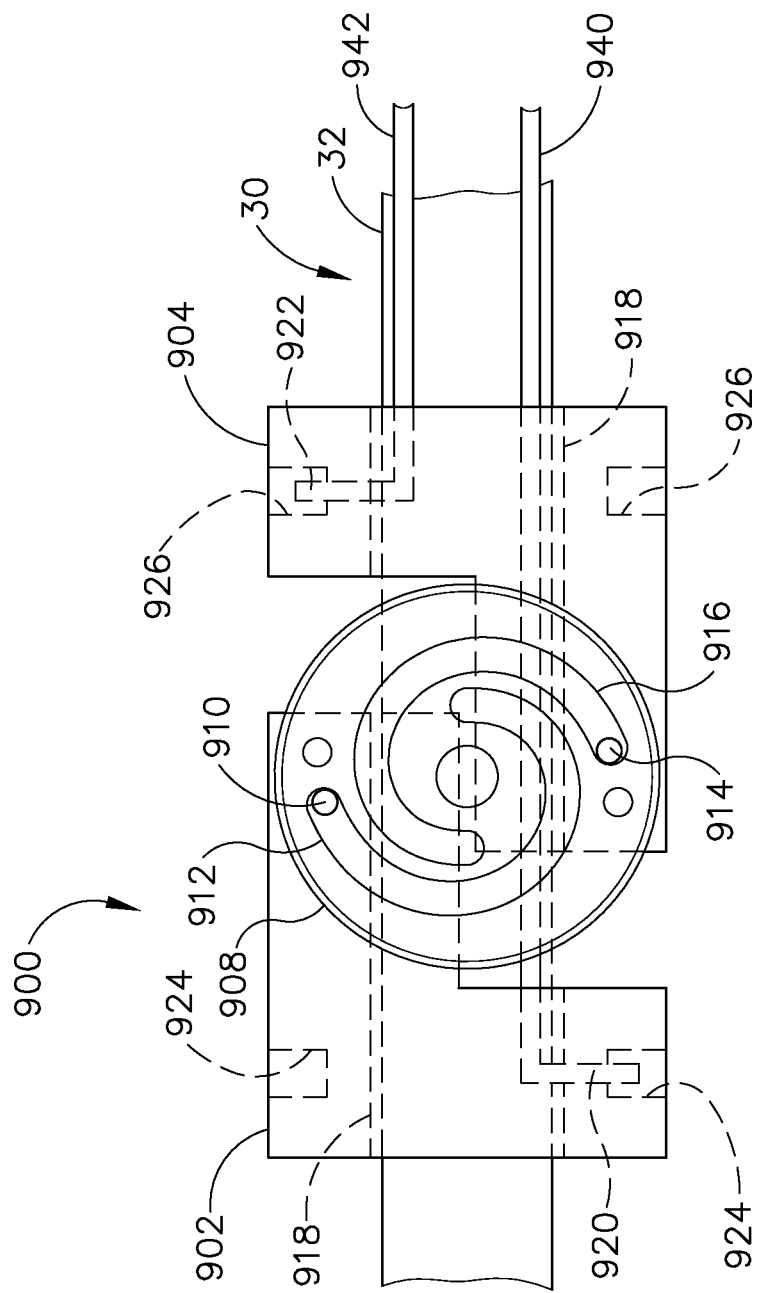
FIG. 30B depicts a partial cross-sectional view of the articulation control assembly of FIG. 29A, taken along line 30B-30B of FIG. 29B, with the articulation control assembly in the second configuration.

As shown in the transition from FIG. 30A to FIG. 30B, knob (906) has been rotated in a direction that has caused cam plate (908) to move counterclockwise. Due to the configuration of cam channels (912, 916), the counterclockwise rotation of cam plate (908) causes pins (910, 914) to follow cam channels (912, 916) such that pin (910) is urged distally while pin (914) is urged proximally. The proximal movement of pin (910) provides proximal movement of collar (902), which in turn causes proximal movement of articulation band (940). The distal movement of pin (914) provides distal movement of collar (904), which in turn causes distal movement of articulation band (942). Thus, articulation bands (940, 942) translate simultaneously in opposing longitudinal directions in response to rotation of knob (906). Rotation of knob (906) will thereby change the articulation state of articulation section (130).

It should be understood that pins (910, 914) and cam channels (912, 916) may be positioned and arranged such that rotation of knob (906) in a first angular direction will cause articulation section (130) to deflect in a first lateral direction away from the longitudinal axis of outer sheath (32); while rotation of knob (906) in a second angular direction will cause articulation section (130) to deflect in a second lateral direction away from the longitudinal axis of outer sheath (32). It should also be understood that, due to the configuration and arrangement of pins (910, 914) and cam channels (912, 916), articulation control assembly (900) may provide self-locking of articulation section (130). In other words, friction between pins (910, 914) and cam channels (912, 916) may prevent articulation section (130) from inadvertently deflecting away from a selected state of articulation unless and until the operator rotates knob (906).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body assembly; (b) a shaft extending distally from the body assembly, wherein the shaft defines a longitudinal axis; (c) an acoustic waveguide, wherein the waveguide comprises a flexible portion; (d) an articulation section coupled with the shaft, wherein a portion of the articulation section encompasses the flexible portion of the waveguide; (e) an end effector comprising an ultrasonic blade in acoustic communication with the waveguide; (f) an articulation drive assembly operable to drive articulation of the articulation section to thereby deflect the end effector from the longitudinal axis, wherein the articulation drive assembly comprises an actuator, wherein the actuator is movable relative to the body assembly to drive articulation of the articulation section; and (g) a locking feature in communication with the actuator, wherein the locking feature is movable between an unlocked state and a locked state, wherein the locking feature is configured to permit movement of the actuator relative to the body assembly in the unlocked state, wherein the locking feature is configured to prevent movement of the actuator relative to the body assembly in the locked state.

Example 2

The apparatus of Example 1 or any of the following Examples, wherein the locking feature is resiliently biased into the locked configuration.

Example 3

The apparatus of Example 2, wherein the locking feature is resiliently biased along an axis that is perpendicular to the longitudinal axis.

Example 4

The apparatus of Example 2, wherein the locking feature is resiliently biased along a plane that is parallel to the longitudinal axis.

Example 5

The apparatus of any of the preceding or following Examples, wherein the body assembly comprises an articulation housing, wherein the actuator comprises a knob having a handle and a body portion, wherein the articulation housing is configured to receive the body portion of the knob.

Example 6

The apparatus of Example 5, wherein the locking feature comprises a male detent feature and a female detent feature configured to receive the male detent feature, wherein the male detent feature is disposed on one of the knob or the articulation housing, wherein the female detent feature is disposed on the other of the knob or the articulation housing.

Example 7

The apparatus of Example 6, wherein the knob comprises a plurality of male detent features disposed circumferentially on the knob, wherein the articulation housing comprises a plurality of female detent features configured to correspondingly receive the male detent features.

Example 8

The apparatus of Example 5, wherein knob comprises a movable arm having an end, wherein the end of the movable arm is positioned to engage an engageable portion of the articulation housing in the locked configuration, wherein the end of the movable arm is configured to be spaced from the engageable portion of the articulation housing in the unlocked configuration.

Example 9

The apparatus of Example 5, wherein the housing comprises an inner wall, wherein the locking feature comprises a plurality of first engagement features circumferentially disposed on the inner wall.

Example 10

The apparatus of any of the preceding or following Examples, wherein the locking feature comprises a button extending along an axis of the actuator, wherein the locking feature is configured to move to the unlocked configuration in response to an actuation of the button along the axis.

Example 11

The apparatus of Example 10, wherein the locking feature comprises at least one member operably coupled to the button, wherein the at least one member is biased radially inwardly toward the axis, wherein the member is configured to move radially inwardly in response to actuating the button along the axis.

Example 12

The apparatus of Example 10, wherein the body assembly comprises an articulation housing comprising an inner wall, wherein the articulation housing is configured to receive a portion of the actuator such that the inner wall surrounds a portion of the actuator, wherein the at least one member is configured to engage a portion of the inner wall prior to moving radially inwardly in response to actuating the button along the axis.

Example 13

The apparatus of Example 13, wherein the inner wall comprises a first detent feature, wherein the member comprises a second detent feature, where the first detent feature is complementary to the second detent feature.

Example 14

The apparatus of any of the preceding or following Examples, wherein the locking feature comprises a lever that is movable along a plane that is parallel to the longitudinal axis.

Example 15

The apparatus of any of the preceding or following Examples, wherein the locking feature is configured to prevent movement of the actuator in only one direction.

Example 16

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section, wherein the end effector comprise a working element configured to engage tissue; (e) an articulation drive assembly operable to drive articulation of the articulation section to thereby deflect the end effector from the longitudinal axis, wherein the articulation drive assembly comprises: (i) a first member, (ii) a second member, and (iii) a rotatable member, wherein the first and second members are operable to translate simultaneously in opposite directions to thereby deflect the end effector from the longitudinal axis in response to rotation of the rotatable member relative to the body assembly; and (f) a locking feature movable between a first position and a second position relative to the rotatable member; wherein the locking feature is configured to resist rotation of the rotatable member in the first position; wherein the locking feature is configured to allow rotation of the rotatable member in the second position.

Example 17

The apparatus of Example 16 or any of the following examples, wherein the rotatable member comprises a knob operably coupled to a threaded rod.

Example 18

The apparatus of Example 16 or any of the following examples, wherein the articulation drive assembly comprises a first collar coupled to the first member and a second collar coupled to the second member, wherein the first collar and second collar are movable along the longitudinal axis in response to rotation of the rotatable knob to thereby cause translation of the first and second members.

Example 19

The apparatus of Example 16 or any of the following examples, wherein the locking feature includes at least one pin and at least one cam member operably coupled to the pin.

Example 20

An apparatus for operating on tissue, the apparatus comprising: (a) a body assembly; (b) a shaft extending distally from the body assembly, wherein the shaft defines a longitudinal axis; (c) an acoustic waveguide, wherein the waveguide comprises a flexible portion; (d) an articulation section coupled with the shaft, wherein a portion of the articulation section encompasses the flexible portion of the waveguide, wherein the articulation section further comprises: (i) a first member, and (ii) a second member, wherein the second member is longitudinally translatable relative to the first member; (e) an end effector comprising an ultrasonic blade in acoustic communication with the waveguide; (f) an articulation drive assembly operable to drive articulation of the articulation section to thereby deflect the end effector from the longitudinal axis in the first direction, wherein the articulation drive assembly comprises a knob having a handle portion and a body portion, wherein the body portion of the knob positioned within a housing portion of the body assembly, wherein the body portion of the knob is configured to rotate within the housing portion, wherein the knob is rotatable to drive articulation of the articulation section; and (h) a locking feature, wherein the locking feature is movable between an unlocked state and a locked state, wherein the locking feature is configured to permit rotation of the knob in the unlocked state, wherein the locking feature is configured to prevent rotation of the knob in the locked state.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body assembly;
   (b) a shaft extending distally from the body assembly, wherein the shaft defines a longitudinal axis;
   (c) an acoustic waveguide, wherein the waveguide comprises a flexible portion;
   (d) an articulation section coupled with the shaft, wherein the articulation section is associated with the flexible portion of the waveguide;
   (e) an end effector comprising an ultrasonic blade in acoustic communication with the waveguide;
   (f) an articulation drive assembly operable to drive articulation of the articulation section to thereby deflect the end effector from the longitudinal axis, wherein the articulation drive assembly comprises an actuator and a transmission feature, wherein the actuator is movable relative to the transmission feature to thereby selectively engage or disengage the transmission feature, wherein the actuator is operable to drive articulation of the articulation section via engagement with the transmission feature; and
   (g) a locking feature in communication with the actuator, wherein the locking feature is configured to lock the transmission feature in response to the actuator being disengaged from the transmission feature, wherein the locking feature is configured to unlock the transmission feature in response to the actuator being engaged with the transmission feature.

2. The apparatus of claim 1, wherein the locking feature is resiliently biased to lock the transmission feature.

3. The apparatus of claim 2, wherein the locking feature is resiliently biased along a plane that is parallel to the longitudinal axis.

4. An apparatus for operating on tissue, the apparatus comprising:
   (a) a body assembly;
   (b) a shaft extending distally from the body assembly, wherein the shaft defines a longitudinal axis;
   (c) an articulation section coupled with the shaft;
   (d) an end effector coupled with the articulation section, wherein the end effector comprise a working element configured to engage tissue;
   (e) an articulation drive assembly operable to drive articulation of the articulation section to thereby deflect the end effector from the longitudinal axis, wherein the articulation drive assembly comprises:
      (i) a first member,
      (ii) a second member,
      (iii) a first rotatable member, wherein the first and second members are operable to translate simultaneously in opposite directions to thereby deflect the end effector from the longitudinal axis in response to rotation of the first rotatable member relative to the body assembly, and
      (iv) a second rotatable member, wherein the second rotatable member is configured to move relative to the body assembly to selectively engage the first rotatable member and thereby drive the first rotatable member;
   (f) a locking feature movable with the second rotatable member between a first position and a second position relative to the first rotatable member;
      wherein the locking feature is configured to resist rotation of the first rotatable member in the first position, wherein the second rotatable member is configured to be disengaged from the first rotatable member when the locking feature is in the first position;
      wherein the locking feature is configured to allow rotation of the first rotatable member in the second position, wherein the second rotatable member is configured to be engaged with the first rotatable member when the locking feature is in the second position.

5. An apparatus for operating on tissue, the apparatus comprising:
   (a) a body assembly;
   (b) a shaft extending distally from the body assembly, wherein the shaft defines a longitudinal axis;
   (c) an acoustic waveguide, wherein the waveguide comprises a flexible portion;
   (d) an articulation section coupled with the shaft, wherein a portion of the articulation section is associated with the flexible portion of the waveguide, wherein the articulation section further comprises:
      (i) a first member, and
      (ii) a second member, wherein the second member is longitudinally translatable relative to the first member;
   (e) an end effector comprising an ultrasonic blade in acoustic communication with the waveguide;
   (f) an articulation drive assembly operable to drive articulation of the articulation section to thereby deflect the end effector from the longitudinal axis in a lateral direction, wherein the articulation drive assembly comprises a knob and a transmission gear, wherein the knob is rotatable to rotate the transmission gear to thereby drive articulation of the articulation section; and
   (h) a locking feature, wherein the locking feature is movable between an unlocked state and a locked state, wherein in the unlocked state the knob is configured to engage the transmission gear and the locking feature is configured to disengage the transmission gear to permit rotation of the transmission gear, wherein in the locked state the knob is configured to disengage the transmission gear and the locking feature is configured to engage the transmission gear to prevent rotation of the transmission gear.

* * * * *